(12) United States Patent
Crouthamel et al.

(10) Patent No.: US 7,135,307 B2
(45) Date of Patent: Nov. 14, 2006

(54) GAMMA THREE PROTEASE

(75) Inventors: Ming-Chih Crouthamel, Perkasie, PA (US); Stephen J. Gardell, Woodbridge, CT (US); Qian Huang, Orefield, PA (US); Ming-Tain Lai, Lansdale, PA (US); Yueming Li, Lansdale, PA (US)

(73) Assignee: Merck & Co., Inc., Rahway, NJ (US)

( * ) Notice: Subject to any disclaimer, the term of this patent is extended or adjusted under 35 U.S.C. 154(b) by 431 days.

(21) Appl. No.: 10/486,265

(22) PCT Filed: Aug. 8, 2002

(86) PCT No.: PCT/US02/26969

§ 371 (c)(1),
(2), (4) Date: Feb. 9, 2004

(87) PCT Pub. No.: WO03/018050

PCT Pub. Date: Mar. 6, 2003

(65) Prior Publication Data

US 2005/0065076 A1    Mar. 24, 2005

Related U.S. Application Data

(60) Provisional application No. 60/311,410, filed on Aug. 10, 2001.

(51) Int. Cl.
    C12Q 1/37     (2006.01)
    C12N 9/50     (2006.01)
    A23J 1/00     (2006.01)

(52) U.S. Cl. .................... 435/23; 435/219; 435/69.2; 530/412

(58) Field of Classification Search ............... 435/23, 435/219, 69.2; 530/412
See application file for complete search history.

(56) References Cited

FOREIGN PATENT DOCUMENTS

WO    WO 01/53255    7/2001
WO    WO 03/018050   3/2002

OTHER PUBLICATIONS

Glenner & Wong, "Alzheimer's Disease: Intitial Report of the Purification and Characterization of a Novel Cerebrovascular Amyloid Protein", Biochemical and Biophysical Research Communications, 120:885-890, 1984.
Ponte et al., "A New A4 Amyloid mRNA Contains a Domain Homologous to Serine Proteinase Inhibitors", Nature 331:525-527, 1988.
Tanzi et al., "Protease Inhibitor Domain Encoded by an Amyloid Protein Precursor mRNA Associated with Alzheimer's Disease", Nature, 331:528-530, 1988.
Kitaguchi et al., "Novel Precursor of Alzheimer's Disease Amyloid Protein Shows Protease Inhibitory Activity", Nature, 331:530-532, 1988.
Selkoe, "The Cell Biology of β-Amyloid Precursor Protein and Presenilin in Alzheimer's Disease", Trends in Cell Biology, 8:447-453, 1998.
Selkoe & Wolfe, "In Search of γ-Secretase: Presenilin at the Cutting Edge", Proc. Natl. Acad. Sci. (PNAS), 97:5690-5692, 2000.
DeStrooper et al., "Deficiency of Presenilin-1 Inhibits the Normal Cleavage of Amyloid Precursor Protein", Nature, 391:387-390, 1998.
Wolfe et al., "Two Transmembrane Aspartates in Presenilin-1 Required for Presenilin Endoproteolysis and γ-Secretase Activity", Nature, 398:513-517, 1999.
Kim et al., "Production and Characterization of Monoclonal Antibodies Reactive to Synthetic Cerebrovascular Amyloid Peptide", Neuroscience Research Comm., vol. 2, No. 3, pp. 121-130, 1988.
Kim et al., "Detection and uantitation of Amyloid B-Peptide With 2 Monoclonal Antibodies", Neuroscience Research Comm., vol. 7, No. 2, pp. 113-122, 1990.
Ida et al., "Analysis of Heterogeneous βA4 Peptides in Human Cerebrospinal Fluid and Blood by a Newly Developed Sensitive Western Blot Assay", Journal of Biological Chemistry, 271:22908-22914, 1996.
Esler et al., "Transition-state Analogue Inhibitors of γ-Secretase Bind Directly to Presenilin-1", Nature Cell Biology, 2:428-434, 2000.
Shearman et al., "L-685458, an Aspartyl Protease Transition State Mimic, Is a Potent Inhibitor of Amyloid-β-Protein Precursor γ-Secretase Activity", Biochemistry, American Chemical Society, 39 :8698-8704, 2000.
Clarke & Shearman, "Quantitation of Amyloid-β Peptides in Biological Milieu Using a Novel Homogeneous Time-Resolved Fluorescence (HTRF) Assay", J.of Neuroscience Methods, 102:61-68, 2000.
Yang et al., "Electrochemiluminescence: A New Diagnostic and Research To 1", Bio/Technology, 12:193-194, 1994.
Khorkova et al., "Modulation of Amyloid Precursor Protein Processing by Compounds with Various Mechanisms of Action: Detection by Liquid Phase Electrochemiluminescent System", J. of Neuroscience Methods, 82:159-166, 1998.
Barelli et al., "Characterization of New Polyclonal Antibodies Specific for 40 and 42 Amino Acid-Long Amyloid β-Peptides", Molecular Medicine, 3:695-707, 1997.
Li et al., "Photoactivated γ-Secretase Inhibitors Directed to the Active Site Covalently Label Presenilin 1", Nature, 405:689-694, 2000.
Li et al., "Presenilin 1 is Linked with γ-Secretase Activity in the Detergent Solubilized State", PNAS, vol. 97, (11), 6138-6143, 2000.

(Continued)

Primary Examiner—Tekchand Saidha
(74) Attorney, Agent, or Firm—Joan E. Switzer; Joanne M. Giesser

(57) ABSTRACT

Gamma three protease is provided, a novel aspartyl class protease that is capable of taking part in the processing of amyloid precursor protein (APP) to Aβ peptide. Gamma three protease may be involved in the development and/or progression of Alzheimers disease. Methods of identifying inhibitors of gamma three protease, useful in the prevention or treatment of Alzheimers disease, are disclosed.

19 Claims, 8 Drawing Sheets

OTHER PUBLICATIONS

Zhang et al., "Biochemical Characterization of the Gamma Secretase Activity That Produces Beta Amyloid Peptides", Biochemistry, 40 (16), 5049-5055, 2001.

Zhang et al., "Presenilins Are Required for Gamma-Secretase Cleavage of Beta-App and Transmemberane Cleavage of Notch-1", Nature Cell Biology, 2:463-465, 2000.

Kimberly et al., "The Transmembrane Aspartates in Presenilin 1 and 2 are Obligatory for Gamma-Secretase Activity and Amyloid Beta-Protein Generation", Journal of Biological Chemistry, The American Society of Biological Chemists, 275:3173-3178, 2000.

Armogida et al., "Endogenous Beta-Amyloid Production in Presenilin-Deficient Embryonic Mouse Fibroblasts", Nature Cell Biology, 3:1030-1033, 2001.

```
   1 agtttcctcg gcagcggtag gcgagagcac gcggaggagc gtgcgcgggg gccccgggag
  61 acggcggcgg tggcggcgcg ggcagagcaa ggacgcggcg gatcccactc gcacagcagc
 121 gcactcggtg ccccgcgcag ggtcgcgatg ctgcccggtt tggcactgct cctgctggcc
 181 gcctggacgg ctcgggcgct ggaggtaccc actgatggta atgctggcct gctggctgaa
 241 ccccagattg ccatgttctg tggcagactg aacatgcaca tgaatgtcca gaatgggaag
 301 tgggattcag atccatcagg gaccaaaacc tgcattgata ccaaggaagg catcctgcag
 361 tattgccaag aagtctaccc tgaactgcag atcaccaatg tggtagaagc caaccaacca
 421 gtgaccatcc agaactggtg caagcggggc cgcaagcagt gcaagaccca tccccacttt
 481 gtgattccct accgctgctt agttggtgag tttgtaagtg atgcccttct cgttcctgac
 541 aagtgcaaat tcttacacca ggagaggatg gatgtttgcg aaactcatct tcactggcac
 601 accgtcgcca aagagacatg cagtgagaag agtaccaact tgcatgacta cggcatgttg
 661 ctgccctgcg gaattgacaa gttccgaggg gtagagtttg tgtgttgccc actggctgaa
 721 gaaagtgaca atgtggattc tgctgatgcg gaggaggatg actcggatgt ctggtggggc
 781 ggagcagaca cagactatgc agatgggagt gaagacaaag tagtagaagt agcagaggag
 841 gaagaagtgg ctgaggtgga agaagaagaa gccgatgatg acgaggacga tgaggatggt
 901 gatgaggtag aggaagaggc tgaggaaccc tacgaagaag ccacagagag aaccaccagc
 961 attgccacca ccaccaccac caccacagag tctgtggaag aggtggttcg agttcctaca
1021 acagcagcca gtaccctga tgccgttgac aagtatctcg agacacctgg ggatgagaat
1081 gaacatgccc atttccagaa agccaaagag aggcttgagg ccaagcaccg agagagaatg
1141 tcccaggtca tgagagaatg ggaagaggca gaacgtcaag caaagaactt gcctaaagct
1201 gataagaagg cagttatcca gcatttccag gagaaagtgg aatctttgga acaggaagca
1261 gccaacgaga gacagcagct ggtggagaca cacatggcca gagtggaagc catgctcaat
1321 gaccgccgcc gcctggccct ggagaactac atcaccgctc tgcaggctgt tcctcctcgg
1381 cctcgtcacg tgttcaatat gctaaagaag tatgtccgcg cagaacagaa ggacagacag
1441 cacaccctaa agcatttcga gcatgtgcgc atggtggatc ccaagaaagc cgctcagatc
1501 cggtcccagg ttatgacaca cctccgtgtg atttatgagc gcatgaatca gtctctctcc
1561 ctgctctaca acgtgcctgc agtggccgag gagattcagg atgaagttga tgagctgctt
1621 cagaaagagc aaaactattc agatgacgtc ttggccaaca tgattagtga accaaggatc
1681 agttacggaa acgatgctct catgccatct ttgaccgaaa cgaaaaccac cgtggagctc
1741 cttcccgtga atggagagtt cagcctggac gatctccagc cgtggcattc ttttggggct
1801 gactctgtgc cagccaacac agaaaacgaa gttgagcctg ttgatgcccg ccctgctgcc
1861 gaccgaggac tgaccactcg accaggttct gggttgacaa atatcaagac ggaggagatc
1921 tctgaagtga agatggatgc agaattccga catgactcag gatatgaagt tcatcatcaa
1981 aaattggtgt tctttgcaga agatgtgggt tcaaacaaag gtgcaatcat tggactcatg
2041 gtgggcggtg ttgtcatagc gacagtgatc gtcatcacct tggtgatgct gaagaagaaa
2101 cagtacacat ccattcatca tggtgtggtg gaggttgacg ccgctgtcac cccagaggag
2161 cgccacctgt ccaagatgca gcagaacggc tacgaaaatc caacctacaa gttctttgag
2221 cagatgcaga actagacccc cgccacagca gcctctgaag ttggacagca aaccattgc
2281 ttcactaccc atcggtgtcc atttatagaa taatgtggga agaaacaaac ccgttttatg
2341 atttactcat tatcgccttt tgacagctgt gctgtaacac aagtagatgc ctgaacttga
2401 attaatccac acatcagtaa tgtattctat ctctctttac attttggtct ctatactaca
2461 ttattaatgg gttttgtgta ctgtaaagaa tttagctgta tcaaactagt gcatgaatag
2521 attctctcct gattatttat cacatagccc cttagccagt tgtatattat tcttgtggtt
2581 tgtgacccaa ttaagtccta ctttacatat gctttaagaa tcgatggggg atgcttcatg
2641 tgaacgtggg agttcagctg cttctcttgc ctaagtattc ctttcctgat cactatgcat
2701 tttaaagtta aacattttta agtatttcag atgctttaga gagattttt ttccatgact
2761 gcattttact gtacagattg ctgcttctgc tatatttgtg atataggaat taagaggata
```

FIG.4A

```
2821 cacacgtttg tttcttcgtg cctgttttat gtgcacacat taggcattga gacttcaagc
2881 ttttctttt ttgtccacgt atctttgggt ctttgataaa gaaaagaatc cctgttcatt
2941 gtaagcactt ttacggggcg ggtggggagg ggtgctctgc tggtcttcaa ttaccaagaa
3001 ttctccaaaa caattttctg caggatgatt gtacagaatc attgcttatg acatgatcgc
3061 tttctacact gtattacata aataaattaa ataaaataac cccgggcaag actttctttt
3121 gaaggatgac tacagacatt aaataatcga agtaattttg ggtggggaga agaggcagat
3181 tcaattttct ttaaccagtc tgaagtttca tttatgatac aaaagaagat gaaaatggaa
3241 gtggcaatat aaggggatga ggaaggcatg cctggacaaa cccttctttt aagatgtgtc
3301 ttcaatttgt ataaaatggt gttttcatgt aaataaatac attcttggag gagc
```

FIG.4B

```
MLPGLALLLLAAWTARALEVPTDGNAGLLAEPQIAMFCGRLNMHMNVQNGKWDSDPSGTKTCID
TKEGILQYCQEVYPELQITNVVEANQPVTIQNWCKRGRKQCKTHPHFVIPYRCLVGEFVSDALL
VPDKCKFLHQERMDVCETHLHWHTVAKETCSEKSTNLHDYGMLLPCGIDKFRGVEFVCCPLAEE
SDNVDSADAEEDDSDVWWGGADTDYADGSEDKVVEVAEEEEVAEVEEEEADDDEDDEDGDEVEE
EAEEPYEEATERTTSIATITTTTTESVEEVVRVPTTAASTPDAVDKYLETPGDENEHAHFQKAK
ERLEAKHRERMSQVMREWEEAERQAKNLPKADKKAVIQHFQEKVESLEQEAANERQQLVETHMA
RVEAMLNDRRRLALENYITALQAVPPRPRHVFNMLKKYVRAEQKDRQHTLKHFEHVRMVDPKKA
AQIRSQVMTHLRVIYERMNQSLSLLYNVPAVAEEIQDEVDELLQKEQNYSDDVLANMISEPRIS
YGNDALMPSLTETKTTVELLPVNGEFSLDDLQPWHSFGADSVPANTENEVEPVDARPAADRGLT
TRPGSGLTNIKTEEISEVKMDAEFRHDSGYEVHHQKLVFFAEDVGSNKGAIIGLMVGGVVIATV
IVITLVMLKKKQYTSIHHGVVEVDAAVTPEERHLSKMQQNGYENPTYKFFEQMQN
```

FIG.4C

SEQUENCE LISTING

<160> NUMBER OF SEQ ID NOS: 10

<210> SEQ ID NO 1
<211> LENGTH: 3354
<212> TYPE: DNA
<213> ORGANISM: Human

<400> SEQUENCE: 1

```
agtttcctcg gcagcggtag gcgagagcac gcggaggagc gtgcgcgggg gccccgggag        60
acggcggcgg tggcggcgcg ggcagagcaa ggacgcggcg gatcccactc gcacagcagc       120
gcactcggtg ccccgcgcag ggtcgcgatg ctgcccggtt tggcactgct cctgctggcc       180
gcctggacgg ctcgggcgct ggaggtaccc actgatggta atgctggcct gctggctgaa       240
ccccagattg ccatgttctg tggcagactg aacatgcaca tgaatgtcca gaatgggaag       300
```

-continued

| | |
|---|---|
| tgggattcag atccatcagg gaccaaaacc tgcattgata ccaaggaagg catcctgcag | 360 |
| tattgccaag aagtctaccc tgaactgcag atcaccaatg tggtagaagc caaccaacca | 420 |
| gtgaccatcc agaactggtg caagcggggc cgcaagcagt gcaagaccca tccccacttt | 480 |
| gtgattccct accgctgctt agttggtgag tttgtaagtg atgcccttct cgttcctgac | 540 |
| aagtgcaaat tcttacacca ggagaggatg gatgtttgcg aaactcatct tcactggcac | 600 |
| accgtcgcca aagagacatg cagtgagaag agtaccaact gcatgactac ggcatgttg | 660 |
| ctgccctgcg gaattgacaa gttccgaggg gtagagtttg tgtgttgccc actggctgaa | 720 |
| gaaagtgaca atgtggattc tgctgatgcg gaggaggatg actcggatgt ctggtggggc | 780 |
| ggagcagaca cagactatgc agatgggagt gaagacaaag tagtagaagt agcagaggag | 840 |
| gaagaagtgg ctgaggtgga agaagaagaa gccgatgatg acgaggacga tgaggatggt | 900 |
| gatgaggtag aggaagaggc tgaggaaccc tacgaagaag ccacagagag aaccaccagc | 960 |
| attgccacca ccaccaccac caccacagag tctgtggaag aggtggttcg agttcctaca | 1020 |
| acagcagcca gtaccctga tgccgttgac aagtatctcg agacacctgg ggatgagaat | 1080 |
| gaacatgccc atttccagaa agccaaagag aggcttgagg ccaagcaccg agagagaatg | 1140 |
| tcccaggtca tgagagaatg ggaagaggca gaacgtcaag caaagaactt gcctaaagct | 1200 |
| gataagaagg cagttatcca gcatttccag gagaaagtgg aatctttgga acaggaagca | 1260 |
| gccaacgaga gacagcagct ggtggagaca cacatggcca gagtggaagc catgctcaat | 1320 |
| gaccgccgcc gcctggccct ggagaactac atcaccgctc tgcaggctgt tcctcctcgg | 1380 |
| cctcgtcacg tgttcaatat gctaaagaag tatgtccgcg cagaacagaa ggacagacag | 1440 |
| cacaccctaa agcatttcga gcatgtgcgc atggtggatc ccaagaaagc cgctcagatc | 1500 |
| cggtcccagg ttatgacaca cctccgtgtg atttatgagc gcatgaatca gtctctctcc | 1560 |
| ctgctctaca acgtgcctgc agtggccgag gagattcagg atgaagttga tgagctgctt | 1620 |
| cagaaagagc aaaactattc agatgacgtc ttggccaaca tgattagtga accaaggatc | 1680 |
| agttacggaa acgatgctct catgccatct ttgaccgaaa cgaaaaccac cgtggagctc | 1740 |
| cttcccgtga atggagagtt cagcctggac gatctccagc cgtggcattc ttttggggct | 1800 |
| gactctgtgc cagccaacac agaaaacgaa gttgagcctg ttgatgcccg ccctgctgcc | 1860 |
| gaccgaggac tgaccactcg accaggttct gggttgacaa atatcaagac ggaggagatc | 1920 |
| tctgaagtga gatgatgc agaattccga catgactcag gatatgaagt tcatcatcaa | 1980 |
| aaattggtgt tcttcaga agatgtgggt tcaaacaaag gtgcaatcat ggactcatg | 2040 |
| gtgggcggtg ttgtcatagc gacagtgatc gtcatcacct tggtgatgct gaagaagaaa | 2100 |
| cagtacacat ccattcatca tggtgtggtg gaggttgacg ccgctgtcac cccagaggag | 2160 |
| cgccacctgt ccaagatgca gcagaacggc tacgaaaatc caacctacaa gttctttgag | 2220 |
| cagatgcaga actagacccc cgccacagca gcctctgaag ttggacagca aaaccattgc | 2280 |
| ttcactaccc atcggtgtcc atttatagaa taatgtggga agaaacaaac ccgttttatg | 2340 |
| atttactcat tatcgccttt tgacagctgt gctgtaacac aagtagatgc ctgaacttga | 2400 |
| attaatccac acatcagtaa tgtattctat ctctctttac attttggtct ctatactaca | 2460 |
| ttattaatgg gttttgtgta ctgtaaagaa tttagctgta tcaaactagt gcatgaatag | 2520 |
| attctctcct gattatttat cacatagccc cttagccagt tgtatattat tcttgtggtt | 2580 |
| tgtgacccaa ttaagtccta ctttacatat gctttaagaa tcgatggggg atgcttcatg | 2640 |
| tgaacgtggg agttcagctg cttctcttgc ctaagtattc cttttcctgat cactatgcat | 2700 |

```
tttaaagtta acatttta agtatttcag atgctttaga gagatttttt ttccatgact      2760
gcattttact gtacagattg ctgcttctgc tatatttgtg atataggaat taagaggata      2820
cacacgtttg tttcttcgtg cctgttttat gtgcacacat taggcattga gacttcaagc      2880
ttttcttttt ttgtccacgt atctttgggt ctttgataaa gaaaagaatc cctgttcatt      2940
gtaagcactt ttacggggcg ggtggggagg ggtgctctgc tggtcttcaa ttaccaagaa      3000
ttctccaaaa caatttctg caggatgatt gtacagaatc attgcttatg acatgatcgc      3060
tttctacact gtattacata aataaattaa ataaaataac cccgggcaag acttttcttt      3120
gaaggatgac tacagacatt aaataatcga agtaattttg ggtggggaga agaggcagat      3180
tcaattttct ttaaccagtc tgaagtttca tttatgatac aaaagaagat gaaaatggaa      3240
gtggcaatat aagggatga ggaaggcatg cctggacaaa cccttctttt aagatgtgtc      3300
ttcaatttgt ataaaatggt gttttcatgt aaataaatac attcttggag gagc           3354
```

<210> SEQ ID NO 2
<211> LENGTH: 695
<212> TYPE: PRT
<213> ORGANISM: Human

<400> SEQUENCE: 2

```
Met Leu Pro Gly Leu Ala Leu Leu Leu Ala Ala Trp Thr Ala Arg
  1               5                  10                  15

Ala Leu Glu Val Pro Thr Asp Gly Asn Ala Gly Leu Leu Ala Glu Pro
                20                  25                  30

Gln Ile Ala Met Phe Cys Gly Arg Leu Asn Met His Met Asn Val Gln
                35                  40                  45

Asn Gly Lys Trp Asp Ser Asp Pro Ser Gly Thr Lys Thr Cys Ile Asp
        50                  55                  60

Thr Lys Glu Gly Ile Leu Gln Tyr Cys Gln Glu Val Tyr Pro Glu Leu
65                  70                  75                  80

Gln Ile Thr Asn Val Val Glu Ala Asn Gln Pro Val Thr Ile Gln Asn
                85                  90                  95

Trp Cys Lys Arg Gly Arg Lys Gln Cys Lys Thr His Pro His Phe Val
                100                 105                 110

Ile Pro Tyr Arg Cys Leu Val Gly Glu Phe Val Ser Asp Ala Leu Leu
            115                 120                 125

Val Pro Asp Lys Cys Lys Phe Leu His Gln Glu Arg Met Asp Val Cys
        130                 135                 140

Glu Thr His Leu His Trp His Thr Val Ala Lys Glu Thr Cys Ser Glu
145                 150                 155                 160

Lys Ser Thr Asn Leu His Asp Tyr Gly Met Leu Leu Pro Cys Gly Ile
                165                 170                 175

Asp Lys Phe Arg Gly Val Glu Phe Val Cys Cys Pro Leu Ala Glu Glu
            180                 185                 190

Ser Asp Asn Val Asp Ser Ala Asp Ala Glu Glu Asp Asp Ser Asp Val
        195                 200                 205

Trp Trp Gly Gly Ala Asp Thr Asp Tyr Ala Asp Gly Ser Glu Asp Lys
    210                 215                 220

Val Val Glu Val Ala Glu Glu Glu Val Ala Glu Val Glu Glu Glu Glu
225                 230                 235                 240

Glu Ala Asp Asp Asp Glu Asp Asp Glu Asp Gly Asp Glu Val Glu Glu
                245                 250                 255
```

-continued

```
Glu Ala Glu Glu Pro Tyr Glu Ala Thr Glu Arg Thr Thr Ser Ile
            260                 265                 270
Ala Thr Thr Thr Thr Thr Thr Glu Ser Val Glu Glu Val Val Arg
        275                 280                 285
Val Pro Thr Thr Ala Ala Ser Thr Pro Asp Ala Val Asp Lys Tyr Leu
        290                 295                 300
Glu Thr Pro Gly Asp Glu Asn Glu His Ala His Phe Gln Lys Ala Lys
305                 310                 315                 320
Glu Arg Leu Glu Ala Lys His Arg Glu Arg Met Ser Gln Val Met Arg
                325                 330                 335
Glu Trp Glu Glu Ala Glu Arg Gln Ala Lys Asn Leu Pro Lys Ala Asp
            340                 345                 350
Lys Lys Ala Val Ile Gln His Phe Gln Glu Lys Val Glu Ser Leu Glu
        355                 360                 365
Gln Glu Ala Ala Asn Glu Arg Gln Gln Leu Val Glu Thr His Met Ala
    370                 375                 380
Arg Val Glu Ala Met Leu Asn Asp Arg Arg Arg Leu Ala Leu Glu Asn
385                 390                 395                 400
Tyr Ile Thr Ala Leu Gln Ala Val Pro Pro Arg Pro Arg His Val Phe
                405                 410                 415
Asn Met Leu Lys Lys Tyr Val Arg Ala Glu Gln Lys Asp Arg Gln His
            420                 425                 430
Thr Leu Lys His Phe Glu His Val Arg Met Val Asp Pro Lys Lys Ala
        435                 440                 445
Ala Gln Ile Arg Ser Gln Val Met Thr His Leu Arg Val Ile Tyr Glu
    450                 455                 460
Arg Met Asn Gln Ser Leu Ser Leu Leu Tyr Asn Val Pro Ala Val Ala
465                 470                 475                 480
Glu Glu Ile Gln Asp Glu Val Asp Glu Leu Leu Gln Lys Glu Gln Asn
                485                 490                 495
Tyr Ser Asp Asp Val Leu Ala Asn Met Ile Ser Glu Pro Arg Ile Ser
            500                 505                 510
Tyr Gly Asn Asp Ala Leu Met Pro Ser Leu Thr Glu Thr Lys Thr Thr
        515                 520                 525
Val Glu Leu Leu Pro Val Asn Gly Glu Phe Ser Leu Asp Asp Leu Gln
    530                 535                 540
Pro Trp His Ser Phe Gly Ala Asp Ser Val Pro Ala Asn Thr Glu Asn
545                 550                 555                 560
Glu Val Glu Pro Val Asp Ala Arg Pro Ala Ala Asp Arg Gly Leu Thr
                565                 570                 575
Thr Arg Pro Gly Ser Gly Leu Thr Asn Ile Lys Thr Glu Glu Ile Ser
            580                 585                 590
Glu Val Lys Met Asp Ala Glu Phe Arg His Asp Ser Gly Tyr Glu Val
        595                 600                 605
His His Gln Lys Leu Val Phe Phe Ala Glu Asp Val Gly Ser Asn Lys
    610                 615                 620
Gly Ala Ile Ile Gly Leu Met Val Gly Gly Val Val Ile Ala Thr Val
625                 630                 635                 640
Ile Val Ile Thr Leu Val Met Leu Lys Lys Lys Gln Tyr Thr Ser Ile
                645                 650                 655
His His Gly Val Val Glu Val Asp Ala Ala Val Thr Pro Glu Glu Arg
            660                 665                 670
His Leu Ser Lys Met Gln Gln Asn Gly Tyr Glu Asn Pro Thr Tyr Lys
```

```
                    675                 680                 685

Phe Phe Glu Gln Met Gln Asn
            690                 695

<210> SEQ ID NO 3
<211> LENGTH: 99
<212> TYPE: PRT
<213> ORGANISM: Human

<400> SEQUENCE: 3

Asp Ala Glu Phe Arg His Asp Ser Gly Tyr Glu Val His His Gln Lys
  1               5                  10                  15

Leu Val Phe Phe Ala Glu Asp Val Gly Ser Asn Lys Gly Ala Ile Ile
             20                  25                  30

Gly Leu Met Val Gly Gly Val Val Ile Ala Thr Val Ile Val Ile Thr
         35                  40                  45

Leu Val Met Leu Lys Lys Lys Gln Tyr Thr Ser Ile His His Gly Val
     50                  55                  60

Val Glu Val Asp Ala Ala Val Thr Pro Glu Glu Arg His Leu Ser Lys
 65                  70                  75                  80

Met Gln Gln Asn Gly Tyr Glu Asn Pro Thr Tyr Lys Phe Phe Glu Gln
                 85                  90                  95

Met Gln Asn

<210> SEQ ID NO 4
<211> LENGTH: 48
<212> TYPE: PRT
<213> ORGANISM: Rattus

<400> SEQUENCE: 4

Asp Ala Glu Phe Gly His Asp Ser Gly Phe Glu Val Arg His Gln Lys
  1               5                  10                  15

Leu Val Phe Phe Ala Glu Asp Val Gly Ser Asn Lys Gly Ala Ile Ile
             20                  25                  30

Gly Leu Met Val Gly Gly Val Val Ile Ala Thr Val Ile Val Ile Thr
         35                  40                  45

<210> SEQ ID NO 5
<211> LENGTH: 100
<212> TYPE: PRT
<213> ORGANISM: Human

<400> SEQUENCE: 5

Met Asp Ala Glu Phe Arg His Asp Ser Gly Tyr Glu Val His His Gln
  1               5                  10                  15

Lys Leu Val Phe Phe Ala Glu Asp Val Gly Ser Asn Lys Gly Ala Ile
             20                  25                  30

Ile Gly Leu Met Val Gly Gly Val Val Ile Ala Thr Val Ile Val Ile
         35                  40                  45

Thr Leu Val Met Leu Lys Lys Lys Gln Tyr Thr Ser Ile His His Gly
     50                  55                  60

Val Val Glu Val Asp Ala Ala Val Thr Pro Glu Glu Arg His Leu Ser
 65                  70                  75                  80

Lys Met Gln Gln Asn Gly Tyr Glu Asn Pro Thr Tyr Lys Phe Phe Glu
                 85                  90                  95

Gln Met Gln Asn
            100
```

```
<210> SEQ ID NO 6
<211> LENGTH: 7
<212> TYPE: PRT
<213> ORGANISM: Artificial Sequence
<220> FEATURE:
<223> OTHER INFORMATION: Flag Sequence

<400> SEQUENCE: 6

Asp Tyr Lys Asp Asp Asp Lys
 1               5

<210> SEQ ID NO 7
<211> LENGTH: 108
<212> TYPE: PRT
<213> ORGANISM: Human

<400> SEQUENCE: 7

Met Asp Ala Glu Phe Arg His Asp Ser Gly Tyr Glu Val His His Gln
 1               5                  10                  15

Lys Leu Val Phe Phe Ala Glu Asp Val Gly Ser Asn Lys Gly Ala Ile
                20                  25                  30

Ile Gly Leu Met Val Gly Gly Val Val Ile Ala Thr Val Ile Val Ile
            35                  40                  45

Thr Leu Val Met Leu Lys Lys Lys Gln Tyr Thr Ser Ile His His Gly
    50                  55                  60

Val Val Glu Val Asp Ala Ala Val Thr Pro Glu Glu Arg His Leu Ser
65                  70                  75                  80

Lys Met Gln Gln Asn Gly Tyr Glu Asn Pro Thr Tyr Lys Phe Phe Glu
                85                  90                  95

Gln Met Gln Asn Asp Tyr Lys Asp Asp Asp Lys
            100                 105

<210> SEQ ID NO 8
<211> LENGTH: 32
<212> TYPE: DNA
<213> ORGANISM: Artificial Sequence
<220> FEATURE:
<223> OTHER INFORMATION: PCR Primer

<400> SEQUENCE: 8
ggaattccat atggatgcag aattccgaca tg                                    32

<210> SEQ ID NO 9
<211> LENGTH: 61
<212> TYPE: DNA
<213> ORGANISM: Artificial Sequence
<220> FEATURE:
<223> OTHER INFORMATION: PCR Primer

<400> SEQUENCE: 9
cgcggatccc tatttatcgt catcgtcttt gtagtcgttc tgcatctgct caaagaactt      60
g                                                                      61

<210> SEQ ID NO 10
<211> LENGTH: 327
<212> TYPE: DNA
<213> ORGANISM: Human

<400> SEQUENCE: 10
atggatgcag aattccgaca tgactcagga tatgaagttc atcatcaaaa attggtgttc      60
tttgcagaag atgtgggttc aaacaaaggt gcaatcattg gactcatggt gggcggtgtt    120
```

-continued

```
gtcatagcga cagtgatcgt catcaccttg gtgatgctga agaagaaaca gtacacatcc      180
attcatcatg gtgtggtgga ggttgacgcc gctgtcaccc cagaggagcg ccacctgtcc      240
aagatgcagc agaacggcta cgaaaatcca acctacaagt tctttgagca gatgcagaac      300
gactacaaag acgatgacga taaatag                                          327
```

GAMMA THREE PROTEASE

CROSS-REFERENCE TO RELATED APPLICATIONS

This application claims the benefit of U.S. Provisional Application No. 60/311,410, filed Aug. 10, 2001, the contents of which are incorporated herein by reference in their entirety.

STATEMENT REGARDING FEDERALLY-SPONSORED R&D

Not applicable.

REFERENCE TO MICROFICHE APPENDIX

Not applicable.

FIELD OF THE INVENTION

The present invention is directed to the field of Alzheimer's disease. In particular, the present invention provides a novel aspartyl protease involved in the processing of Alzheimer's precursor protein to the β-amyloid peptide.

BACKGROUND OF THE INVENTION

Alzheimer's disease is a common, chronic neurodegenerative disease, characterized by a progressive loss of memory and sometimes severe behavioral abnormalities, as well as an impairment of other cognitive functions that often leads to dementia and death. It ranks as the fourth leading cause of death in industrialized societies after heart disease, cancer, and stroke. The incidence of Alzheimer's disease is high, with an estimated 2.5 to 4 million patients affected in the United States and perhaps 17 to 25 million worldwide. Moreover, the number of sufferers is expected to grow as the population ages.

A characteristic feature of Alzheimer's disease is the presence of large numbers of insoluble deposits, known as amyloid plaques, in the brains of those affected. Autopsies have shown that amyloid plaques are found in the brains of virtually all Alzheimer's patients and that the degree of amyloid plaque deposition correlates with the degree of dementia (Cummings & Cotman, 1995, Lancet 326:1524–1587). While some opinion holds that amyloid plaques are a late stage by-product of the disease process, the consensus view is that amyloid plaques are more likely to be intimately, and perhaps causally, involved in Alzheimer's disease.

A variety of experimental evidence supports this view. For example, Aβ, a primary component of amyloid plaques, is toxic to neurons in culture and transgenic mice that overproduce Aβ in their brains show significant deposition of Aβ into amyloid plaques and significant neuronal toxicity (Yankner, 1990, Science 250:279–282; Mattson et al., 1992, J. Neurosci. 12:379–389; Games et al., 1995, Nature 373:523–527; LaFerla et al., 1995, Nature Genetics 9:21–29). Mutations in the APP gene, leading to increased Aβ production, have been linked to heritable forms of Alzheimer's disease (Goate et al., 1991, Nature 349:704–706; Chartier-Harlan et al., 1991, Nature 353:844–846; Murrel et al., 1991, Science 254:97–99; Mullan et al., 1992, Nature Genetics 1:345–347). Presenilin-1 (PS1) and presenilin-2 (PS2) related familial early-onset Alzheimer's disease (FAD) shows disproportionately increased production of Aβ1-42, the 42 amino acid isoform of Aβ, as opposed to Aβ1-40, the 40 amino acid isoform (Scheuner et al, 1996, Nature Medicine 2:864–870). The longer isoform of Aβ is more prone to aggregation than the shorter isoform (Jarrett et al, 1993, Biochemistry 32:4693–4697). Injection of the insoluble, fibrillar form of Aβ into monkey brains results in the development of pathology (neuronal destruction, tau phosphorylation, microglial proliferation) that closely mimics Alzheimer's disease in humans (Geula et al., 1998, Nature Medicine 4:827–831). See Selkoe, 1994, J. Neuropathol. Exp. Neurol. 53:438–447 for a review of the evidence that amyloid plaques have a central role in Alzheimer's disease.

Aβ, a 39–43 amino acid peptide derived by proteolytic cleavage of the amyloid precursor protein (APP), is the major component of amyloid plaques (Glenner & Wong, 1984, Biochem. Biophys. Res. Comm. 120:885–890). APP is actually a family of polypeptides produced by alternative splicing from a single gene. Major forms of APP are known as $APP_{695}$, $APP_{751}$, and $APP_{770}$, with the subscripts referring to the number of amino acids in each splice variant (Ponte et al., 1988, Nature 331:525–527; Tanzi et al., 1988, Nature 331:528–530; Kitaguchi et al., 1988, Nature 331:530–532). APP is membrane bound and undergoes proteolytic cleavage by at least two pathways. In one pathway, cleavage by an enzyme known as α-secretase occurs while APP is still in the trans-Golgi secretory compartment (Kuentzel et al., 1993, Biochem J. 295:367–378). This cleavage by α-secretase occurs within the Aβ portion of APP, thus precluding the formation of Aβ. In another proteolytic pathway, cleavage of the $Met_{671}$-$Asp_{672}$ bond (numbered according to the 751 amino acid protein) by an enzyme known as β-secretase occurs. This cleavage by β-secretase generates the N-terminus of Aβ. The C-terminus is formed by cleavage by a second enzyme known as γ-secretase. The C-terminus is actually a heterogeneous collection of cleavage sites rather than a single site since γ-secretase activity occurs over a short stretch of APP amino acids rather than at a single peptide bond. Peptides of 40 or 42 amino acids in length (Aβ1-40 and Aβ1-42, respectively) predominate among the C-termini generated by γ-secretase. Aβ1-42 is more prone to aggregation than Aβ1-40, is the major component of amyloid plaque (Jarrett et al., 1993, Biochemistry 32:4693–4697; Kuo et al., 1996, J. Biol. Chem. 271:4077–4081), and its production is closely associated with the development of Alzheimer's disease (Sinha & Lieberburg, 1999, Proc. Natl. Acad. Sci. USA 96:11049–11053). The bond cleaved by γ-secretase appears to be situated within a transmembrane domain of APP. It is unclear as to whether the C-termini of Aβ1-40 and Aβ1-42 are generated by a single γ-secretase protease with sloppy specificity or by two distinct proteases. For a review that discusses APP and its processing, see Selkoe, 1998, Trends Cell. Biol. 8:447–453.

Much interest has focused on the possibility of inhibiting the development of amyloid plaques as a means of preventing or ameliorating the symptoms of Alzheimer's disease. To that end, a promising strategy is to inhibit the activity of β- and γ-secretase, the two enzymes that together are responsible for producing Aβ. This strategy is attractive because, if the formation of amyloid plaques as a result of the deposition of Aβ is a cause of Alzheimer's disease, inhibiting the activity of one or both of the two secretases would intervene in the disease process at an early stage, before late-stage events such as inflammation or apoptosis occur. Such early stage intervention is expected to be particularly beneficial (see, e.g., Citron, 2000, Molecular Medicine Today 6:392–397).

To that end, various assays have been developed that are directed to the identification of compounds that may interfere with the production of Aβ or its deposition into amyloid plaques. U.S. Pat. No. 5,441,870 is directed to methods of monitoring the processing of APP by detecting the production of amino terminal fragments of APP. U.S. Pat. No. 5,605,811 is directed to methods of identifying inhibitors of the production of amino terminal fragments of APP. U.S. Pat. No. 5,593,846 is directed to methods of detecting soluble Aβ by the use of binding substances such as antibodies. Esler et al., 1997, Nature Biotechnology 15:258–263 described an assay that monitored the deposition of Aβ from solution onto a synthetic analogue of an amyloid plaque. The assay was suitable for identifying compounds that could inhibit the deposition of Aβ. However, this assay is not suitable for identifying substances, such as inhibitors of γ-secretase, that would prevent the formation of Aβ. Thus, the assay of Esler is directed to a step that is further along in the formation of amyloid plaque than is the assay described in this application.

Various groups have cloned and sequenced cDNA encoding a protein that is believed to be β-secretase (Vassar et al., 1999, Science 286:735–741; Hussain et al., 1999, Mol. Cell. Neurosci. 14:419–427; Yan et al., 1999, Nature 402:533–537; Sinha et al., 1999, Nature 402:537–540; Lin et al., 2000, Proc. Natl. Acad. Sci. USA 97:1456–1460) but the identity of γ-secretase has been more elusive. A pair of proteins known as presenilin-1 and presenilin-2 are viewed as possible candidates (Selkoe & Wolfe, 2000, Proc. Natl. Acad. Sci. USA 97:5690–5692).

Presenilin-1 (PS1) and presenilin-2 (PS2) are polytopic membrane proteins that are involved in γ-secretase-mediated processing of APP. The most common cause of familial early-onset Alzheimer's disease is the autosomal dominant inheritance of assorted mutations in the PSi gene (Sherrington et al., 1995, Nature 375:754–760). These PSi mutations lead to increased production of Aβ1-42 (Scheuner et al., 1996, Nature Medicine 2:864–870; Duff et al., 1996, Nature 383:710–713; Borchelt et al., 1996, Neuron 17:1005–1013). Similarly, certain mutations in PS2 cause familial early-onset Alzheimer's disease and increased generation of Aβ1-42 (Levy-Lahad et al., 1995, Science 269: 970–973). Cultured isolated neurons from PS1-deficient mice exhibit reduced γ-secretase-mediated cleavage of APP (De Strooper et al., 1998, Nature 391:387–390). It was suggested that PS1 might influence trafficking of APP and/or γ-secretase or it might play a more direct role in proteolytic cleavage of APP. Directed mutagenesis of two conserved transmembrane-situated aspartates in PS1 was shown to inactivate γ-secretase activity in cellular assays, suggesting that PS1 is either a required diaspartyl cofactor for γ-secretase or is itself γ-secretase, an intramembranous aspartyl protease (Wolfe et al., 1999, Nature 398:513–517). Moreover, Li et al., 2000, Nature 405:689–694 made photoactivatable derivatives of a highly specific and potent aspartyl protease transition state analog inhibitor and found that the inhibitor selectively labeled presenilin fragments.

Despite results such as those described above, it is still uncertain whether PS1 and PS2 are responsible for the γ-secretase activity that is relevant to the processing of APP in connection with Alzheimer's disease. It is desirable to identify all the proteases that may have γ-secretase activity and thus may be involved in the development of Alzheimer's disease. Therefore, the identification and purification of novel proteins possessing γ-secretase activity is valuable. The availability of such novel proteases would allow for the development of assays to discover inhibitors of such proteases. Such inhibitors are likely to be valuable in the treatment of Alzheimer's disease.

SUMMARY OF THE INVENTION

The present invention is directed to γ3 protease, a novel aspartyl class protease that is capable of taking part in the processing of amyloid precursor protein (APP) to Aβ peptide. Since the deposition of Aβ in the brains of patients suffering from Alzheimer's disease is believed to play an important role in the development of this disease, γ3 protease may be involved in the development and/or progression of Alzheimer's disease. Therefore, inhibitors of γ3 protease may have utility in the prevention or treatment of Alzheimer's disease. Methods of identifying such inhibitors are disclosed.

Also disclosed are membrane preparations containing partially purified γ3 protease as well as methods of further purifying γ3 protease and identifying cDNA encoding γ3 protease.

BRIEF DESCRIPTION OF THE DRAWINGS

FIG. 4A–B shows the cDNA sequence (SEQ.ID.NO.:1) and FIG. 4C shows the amino acid sequence (SEQ.ID.NO.:2) of the 695 amino acid splice variant of wild-type Alzheimer's precursor protein (APP). See GenBank accession no. Y00264 and Kang et al., 1987, Nature 325:733–736.

Figure 5:
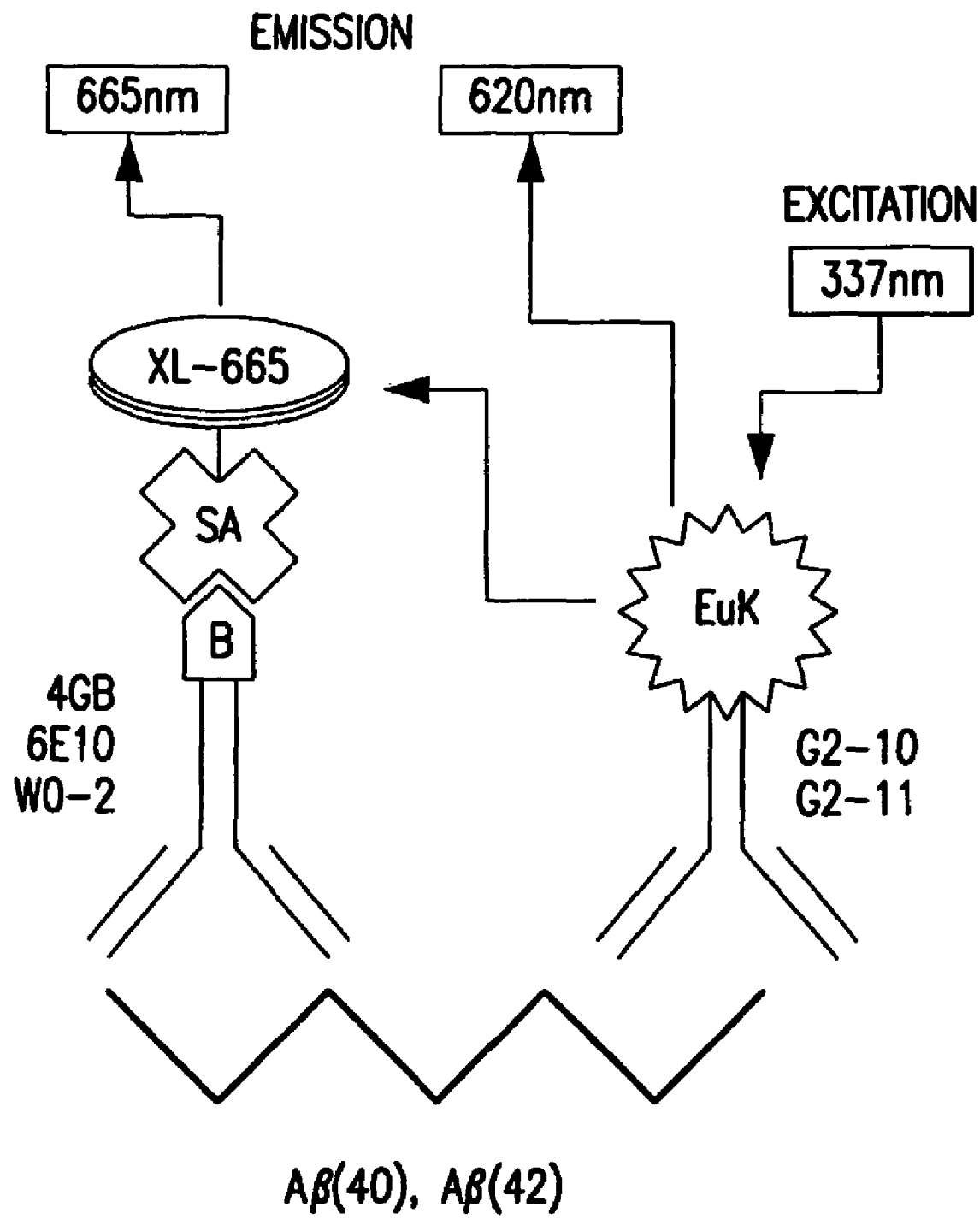
FIG. 5 shows a schematic representation of the HTRF method of detection described herein. In this embodiment, the first antibody is either 4G8, 6E10, or WO-2. The second antibody is either G2-10 (which specifically detects Aβ1-40) or G2-11 (which specifically detects Aβ1-42). The epitopes recognized by these antibodies are shown in FIG. 6. The first antibody is coupled to XL-665 by a streptavidin/biotin link. Specific signal generation, indicating γ3 protease cleavage of the substrate, occurs when Europium cryptate (EuK)- coupled G2-10 or G2-11 (second antibodies) and the first antibody-biotin-streptavidin-XL-665 pair are brought into proximity as a result of binding to the Aβ peptide. This results in fluorescence resonance energy transfer (FRET) from EuK to XL-665.
Figure 6:
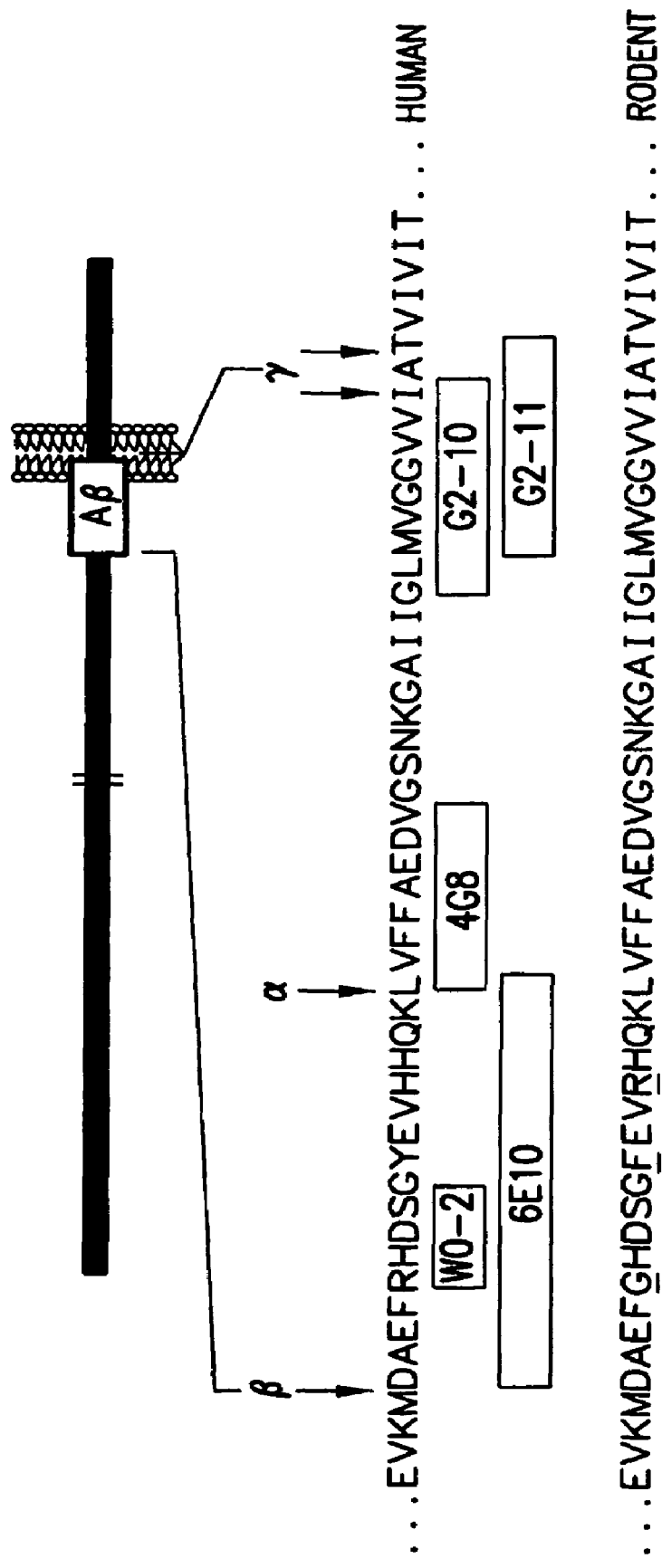

FIG. 6 shows the epitopes recognized by the monoclonal antibodies of FIG. 5. The solid bars indicate the amino acid sequences against which the monoclonal antibodies were raised, or, where determined, their recognition epitopes (Kim et al., 1988, Neurosci. Res. Comm. 2:121–130; Kim et al., 1990, Neurosci. Res. Comm. 7:113–122; Ida et al., 1996, J. Biol. Chem. 271:22908–22914). The human and rodent Aβ sequences are shown with the three amino acid differences between them underlined in the rodent sequence. The major cleavage sites of the APP molecule by the various secretases are indicated by arrows: β=β secretase; α=α secretase; γ=γ secretase and γ3 protease.

DETAILED DESCRIPTION OF THE INVENTION

For the purposes of this invention:

"Substances" can be any substances that are generally screened in the pharmaceutical industry during the drug development process. For example, substances may be low molecular weight organic compounds (e.g., having a molecular weight of less than about 2,000 daltons and preferably less than about 1,000 daltons), RNA, DNA, antibodies, peptides, or proteins.

The conditions under which substances are employed in the methods described herein are conditions that are typically used in the art for the study of protein-ligand interactions: e.g., salt conditions such as those represented by such commonly used buffers as PBS or in tissue culture media; a temperature of about 4° C. to about 55° C.; incubation times of from several seconds to several hours. The pH can be a pH at which the activity of γ3 protease can be distinguished from the activity of γ-secretase, e.g., a pH of about 5.8 to 6.2. Alternatively, the pH can be closer to pH 7.0, a pH at which γ-secretase is active, if the methods are run in the presence of a γ-secretase inhibitor.

The present invention relates to a novel, membrane-bound aspartyl class protease, γ3 protease. γ3 protease is an aspartyl class protease since its activity is inhibited by pepstatin A. γ3 protease cleaves Alzheimer's precursor protein (APP), as well as artificial substrates incorporating portions of APP, at the same or similar sites as γ-secretase. Since cleavage of APP by γ-secretase is thought to be an essential step in the generation of Aβ peptide, γ3 protease may also be involved in the generation of Aβ. Thus, γ3 protease, like γ-secretase, may play a role in the development and/or progression of Alzheimer's disease.

The activity of γ3 protease can be distinguished from the known γ secretase activity involving presenilin-1 and presenilin-2 by the following characteristics:

γ3 protease activity migrates with an $M_r$ of approximately 60 kDa to 120 kDa during gel filtration analysis while the corresponding $M_r$ of the γ secretase complex containing presenilin-1 is approximately $2\times10^6$ kDa.

γ3 protease activity is not susceptible to inhibition by L-685,458 while the activity of the γ secretase complex containing presenilin-1 or presenilin-2 is inhibited by L-685,458.

γ3 protease activity displays a pH optimum of 6.0 while the activity of the γ secretase complex containing presenilin-1 or presenilin-2 displays a pH optimum of 6.8.

γ3 protease activity is present in presenilin-1/presenilin-2 double knockout cells.

γ3 protease proteolytic products are dominated by Aβ1-42, which is more prone to aggregate and form Aβ plaques than Aβ1-40.

The present invention provides assays for γ3 protease. In broad terms, such assays comprise providing a source of γ3 protease, incubating the γ3 protease in the presence of a suitable substrate under suitable conditions such that the γ3 protease can cleave the substrate into product, and determining the presence and/or the amount of product produced from the substrate by the γ3 protease.

The source of the γ3 protease may be a preparation of purified protein, but can also be cells that express γ3 protease, or membranes from such cells. In certain embodiments, the cells recombinantly express γ3 protease. That is, they have been transfected with an expression vector encoding γ3 protease such that the expression vector directs the expression of γ3 protease in the cells. Preferably, the recombinant cells do not naturally express γ3 protease, or at least, express γ3 protease to only an insignificant level as compared to the level achieved via recombinant expression.

A variety of host cells are suitable for recombinant expression of γ3 protease. Particularly preferred are mammalian cell lines. In particular embodiments, the test cells and control cells are selected from the group consisting of: L cells L-M(TK⁻) (ATCC CCL 1.3), L cells L-M (ATCC CCL 1.2), HEK293 (ATCC CRL 1573), Raji (ATCC CCL 86), CV-1 (ATCC CCL 70), COS-1 (ATCC CRL 1650), COS-7 (ATCC CRL 1651), CHO-K1 (ATCC CCL 61), 3T3 (ATCC CCL 92), NIH/3T3 (ATCC CRL 1658), HeLa (ATCC CCL 2), C127I (ATCC CRL 1616), BS-C-1 (ATCC CCL 26), T24 (ATCC HTB4), and MRC-5 (ATCC CCL 171).

In preferred embodiment, the source of γ3 protease is cells derived from presenilin-1/presenilin-2 double knockout mice. These mice have had both their presenilin-1 and presenilin-2 genes disrupted so that cells from these mice cannot express functional presenilin-1 or presenilin-2. Thus, these cells have no γ-secretase activity that is due to presenilin-1 or presenilin-2.

The source of γ3 protease can be suitable membrane preparations from cells that express γ3 protease. Such membrane preparations can be obtained by procedures, such as that described in Example 1, comprising:

(a) lysis of the cells;
(b) low speed centrifugation to remove unbroken cells and large subcellular structures;
(c) high speed centrifugation of the supernatant from step (b) to pellet membranes containing γ3 protease;
(d) resuspension of the membranes from step (c);
(e) assaying the resuspended membranes of step (d) for γ3 protease activity.

In particular embodiments, low speed centrifugation is carried out by centrifuging at from about 750×g to about 1,500×g; preferably from about 900×g to about 1,200×g; and most preferably at about 1,000×g at a temperature of about 2° C. to about 10° C., preferably from about 3° C. to about 6° C., and most preferably at about 4° C. for about 5 minutes to about 20 minutes, preferably for about 8 minutes to about 15 minutes, and most preferably for about 10 minutes. The low speed centrifugation step may be repeated if desired.

In particular embodiments, high speed centrifugation is carried out by centrifuging from about 75,000×g to about 150,000×g; preferably from about 90,000×g to about 120,000×g; and most preferably at about 100,000×g at a temperature of about 2° C. to about 10° C., preferably from about 3° C. to about 6° C., and most preferably at about 4° C. for about 30 minutes to about 90 minutes, preferably for about 50 minutes to about 75 minutes, and most preferably for about 60 minutes.

In particular embodiments, resuspension of the membranes is carried out by use of a Douce Homogenizer.

Solubilized, purified γ3 protease can be obtained from such membrane preparations. Recovery of soluble γ3 protease activity may be achieved using a zwitterionic detergent to extract the membrane preparation followed by suitable steps to isolate the solubilized γ3 protease.

Accordingly, the present invention includes a method of purifying γ3 protease comprising:
  (a) preparing membranes containing 3 protease;
  (b) solubilizing the membranes in a zwitterionic detergent;
  (c) centrifuging the solubilized membranes to obtain a supernatant;
  (d) passing the supernatant over an affinity column to bind γ3 protease in the supernatant to the affinity column;
  (e) eluting γ3 protease from the affinity column.

In particular embodiments, the amount of zwitterionic detergent is about 1% to about 2% (w/v). Examples of zwitterionic detergents include CHAPSO and CHAPS.

In particular embodiments, the affinity column is a Pepstatin A affinity column.

In particular embodiments, the centrifuging is carried out by centrifuging from about 75,000×g to about 150,000×g; preferably from about 90,000×g to about 120,000×g; and most preferably at about 100,000×g at a temperature of about 2° C. to about 10° C., preferably from about 3° C. to about 6° C., and most preferably at about 4° C. for about 30 minutes to about 90 minutes, preferably for about 50 minutes to about 75 minutes, and most preferably for about 60 minutes. A suitable instrument for such centrifugation is a BECKMAN XL-90 Ultracentrifuge.

Examples of cells expressing γ3 protease include HeLa S3, human embryonic kidney (HEK293) cells and Chinese hamster ovary (CHO) cells. Preferred cells producing γ3 protease are presenilin-1 (PS-1)/presenilin-2 (PS-2) double knockout cells that have both copies of both PS-1 and PS-2 disabled. These PS-1/PS-2 double knockout cells thus have no PS-1 and PS-2 activity. Such cells can be derived from embryonic stem cells obtained from the embryos of the founders from cross breeding transgenic mice (PS1 knock-out and PS2 knock-out mice).

γ3 protease recognizes and cleaves substrates that have the amino acid sequence of APP in the vicinity of the γ-secretase cleavage sites. For APP695, these γ-secretase cleavage sites are predominately between positions 635 and 636 (to produce (Aβ1-40) or between positions 637 and 638 (to produce (Aβ1-42). Shown immediately below is SEQ.ID.NO.:3, which consists of the relevant portions of human APP (SEQ.ID.NO.:2), beginning at position 1 of Aβ. The predominant γ3 protease cleavage sites are indicated by arrows.

DAEFRHDSGYEVHHQKLVFFAEDVGSNKGAII (SEQ. ID. NO.: 3)

↓ ↓
GLMVGGVV IA TVIVITLVMLKKKQYTSIHH

GVVEVDAAVTPEERHLSKMQQNGYENPTYKFF

EQMQN

Cleavage at the left arrow (between positions 40 and 41 of SEQ.ID.NO.:3) gives rise to Aβ1-40 while cleavage at the right arrow (between positions 42 and 43 of SEQ.ID.NO.:3) gives rise to Aβ1-42.

Suitable substrates of γ3 protease include polypeptides comprising an amino acid sequence from the vicinity of these cleavage sites. For example, suitable substrates would include polypeptides comprising all of SEQ.ID.NO.:3; polypeptides comprising positions 10–70 of SEQ.ID.NO.:3; polypeptides comprising positions 15–65 of SEQ.ID.NO.:3; polypeptides comprising positions 20–60 of SEQ.ID.NO.:3; polypeptides comprising positions 25–55 of SEQ.ID.NO.:3; polypeptides comprising positions 30–50 of SEQ.ID.NO.:3; polypeptides comprising positions 31–49 of SEQ.ID.NO.:3; polypeptides comprising positions 32–48 of SEQ.ID.NO.:3; polypeptides comprising positions 33–47 of SEQ.ID.NO.:3; polypeptides comprising positions 34–46 of SEQ.ID.NO.:3; polypeptides comprising positions 35–45 of SEQ.ID.NO.:3; and polypeptides comprising positions 36–44 of SEQ.ID.NO.:3.

Corresponding polypeptides from versions of APP from mammals other than humans are also suitable substrates. Shown immediately below is SEQ.ID.NO.:4, which consists of the relevant portion of APP from rodents, e.g., rats and mice.

DAEFGHDSGFEVRHQKLVFFAEDVGSNKGAII (SEQ. ID. NO.: 4)

↓ ↓
GLMVGGVV IA TVIVIT

This rodent sequence differs from the human sequence at the three underlined residues.

The substrate for γ3 protease may be full-length APP, either wild-type or one of the various mutants forms of APP, or some subset of the amino acids of APP that contains the γ-secretase cleavage sites. A cDNA sequence encoding full length wild-type APP is shown in FIG. 4A–B and is SEQ.ID.NO.:1 while the amino acid sequence of full length wild-type APP is shown in FIG. 4C and is SEQ.ID.NO.:2. APP may be provided by recombinantly expressing cDNA encoding APP in suitable host cells and purifying the APP by methods well known in the art. Alternatively, APP may be produced by in vitro coupled transcription/translation systems that are also well known in the art.

APP may also be provided as a γ3 protease substrate without purification. Cells expressing APP, either naturally or through recombinant means, are used directly, by exposing such cells to substances that are to be tested in the assays of the present invention without first purifying or isolating APP from the cells. The production of suitable γ3 protease cleavage products from the APP in the cells is then measured or detected.

In certain embodiments of the assays of the present invention, where the assay system is expected to contain γ-secretase activity associated with presenilin-1 or presenilin-2, it is advantageous to run the assay under conditions that inhibit the presenilin-1 or presenilin-2-associated γ-secretase activity. Such conditions include running the assay in the presence of an inhibitor of the presenilin-1/presenilin-2-associated γ-secretase activity (e.g., L-685,458) and/or running the assay at a pH of about 6.0 (a pH at which the activity of presenilin-1/presenilin-2-associated γ-secretase is minor but which is optimum for γ3 protease).

In certain embodiments, the inhibitor of the presenilin-1/presenilin-2-associated γ-secretase activity is a transition-state analogue inhibitor of γ-secretase. Esler et al., 2000, Nature Cell Biol. 2:428–434 disclose a series of such inhibitors, including methods of synthesis of the inhibitors. The structure of this series of inhibitors is shown in Example 13. The disclosures of Esler et al., 2000, Nature Cell Biol. 2:428–434 are incorporated herein by reference, in their entirety.

Another series of transition-state analogue inhibitors is described in International Patent Publication WO 01/53255. This series includes the inhibitor L-685,458 (see Example 8). Representative members of this series are shown in Example 14. L-685,458 is also disclosed in Shearman et al., 2000, Biochemistry 39:8698–8704. The disclosures of International Patent Publication WO 01/53255 and Shearman et al., 2000, Biochemistry 39:8698–8704 are incorporated herein by reference, in their entirety.

A particular embodiment of the assays of the present invention is a method of identifying inhibitors of the activity of γ3 protease. Such a method comprises:

(a) incubating:
  (i) a source γ3 protease;
  (ii) a substrate of γ3 protease:
  in the presence and in the absence of a substance;
(b) determining whether the substrate has been cleaved by the γ3 protease;

where, if the substrate has been cleaved by γ3 protease to a lesser extent in the presence as compared to the absence of the substance, then the substance is an inhibitor of γ3 protease.

The method of identifying inhibitors of γ3 protease can be used to screen libraries of substances or other sources of substances to identify substances that are inhibitors of the activity of γ3 protease. Such identified inhibitory substances can serve as "leads" for the development of pharmaceuticals that can be used to treat patients having Alzheimer's disease.

In certain embodiments, the assays of the present invention employ an artificial substrate derived from APP. One particular version of such a γ3 protease substrate is a fusion protein comprising a carboxy-terminal fragment of APP (a "β-CTF domain") and a hydrophilic polypeptide moiety. The β-CTF domain provides a polypeptide that can be cleaved by γ3 protease activity. The hydrophilic polypeptide moiety allows for the β-CTF domain to be cleaved by detergent-solubilized γ3 protease by promoting substrate solubility. The β-CTF domain approximates the C-terminal fragment of APP after cleavage by β-secretase or is a functional derivative thereof.

SEQ.ID.NO.:5 provides an example of a β-CTF domain. SEQ.ID.NO.:5 is a naturally occurring sequence corresponding to the β-CTF portion of APP (amino acids 596–695) along with an N-terminus methionine. The N-terminus methionine facilitates recombinant production of the substrate. SEQ.ID.NO.:5 is as follows:

MDAEFRHDSGYEVHHQKLVFFAEDVGSNKGAI (SEQ. ID. NO.: 5)

IGLMVGGVVIATVIVITLVMLKKKQYTSIHHG

VVEVDAAVTPEERHLSKMQQNGYENP TYKFF

EQMQN

The second component of the γ3 protease substrate, the hydrophilic polypeptide moiety, is preferably chosen to increase the solubility of the γ3 protease substrate in a zwitterionic detergent. Hydrophilic moieties can be obtained by taking into account the known charges and polarity of different amino acid R groups. Preferably, the presence of the hydrophilic moiety does not result in a substrate having a substantial decrease in activity.

Different embodiments concerning the overall length and charge of the hydrophilic moiety are provided as follows: in different embodiments concerning the length, the length is about 5 to about 20 amino acids, about 8 to about 12 amino acids, or about 8 amino acids; in different embodiments concerning the overall charge, the charge is greater than ±2, ±3, or ±4. With respect to a negative charge, a greater charge indicates a higher negative charge value.

Preferably, the hydrophilic moiety comprises, consists essentially of, or consists of, a polypeptide substantially identical to SEQ.ID.NO.:6: DYKDDDDK. Substantially identical to SEQ.ID.NO.:6 indicates that within a corresponding 8 amino acid stretch (no gaps) there is a two, one, or zero amino acid difference. Preferably, the hydrophilic moiety consists of the amino acid sequence of SEQ.ID.NO.:6.

In an embodiment of the present invention, the γ3 protease substrate comprises, consists essentially of, or consists of, a sequence substantially similar to SEQ.ID.NO.:7. SEQ.ID.NO.:7 corresponds to SEQ.ID.NO.:5 along with a carboxyl terminal SEQ.ID.NO.:6 sequence. Preferably, the γ3 protease substrate comprises, consists essentially of, or consists of SEQ.ID.NO.:7.

MDAEFRHDSGYEVHHQKLVFFAEDVGSNKGAI (SEQ. ID. NO.: 7)

IGLMVGGVVIATVIVITLVMLKKKQYTSIHHG

VVEVDAAVTPEERHLSKMQQNGYENPTYKFFE

QMQNDYKDDDDK

Based on the disclosure provided herein γ3 protease substrates can be produced using standard biochemical synthesis and recombinant nucleic acid techniques. Techniques for chemical synthesis of polypeptides are well known in the art. (See, for example, Vincent, in *Peptide and Protein Drug Delivery*, New York, N.Y., Dekker, 1990). Recombinant synthesis techniques for polypeptides are also well known in the art. Such techniques employ a nucleic acid template for polypeptide synthesis. Starting with a particular amino acid sequence and the known degeneracy of the genetic code, a large number of different encoding nucleic acid sequences can be obtained that encode the desired γ3 protease substrate.

Recombinant synthesis of polypeptides that are γ3 protease substrates can be achieved in a host cell using an expression vector. An expression vector contains recombinant nucleic acid encoding a desired polypeptide along with regulatory elements for proper transcription and processing. Generally, the regulatory elements that are present in an expression vector include a transcriptional promoter, a ribosome binding site, a terminator, and an optionally present operator. A preferred element is a polyadenylation signal providing for processing in eukaryotic cells. Other preferred elements include an origin of replication for autonomous replication in a host cell, a selectable marker, a limited number of useful restriction enzyme sites, and a potential for high copy number. Examples of expression vectors are cloning vectors, modified cloning vectors, specifically designed plasmids, and viruses.

A variety of expression vectors can be used. Commercially available expression vectors which are suitable include, but are not limited to, pMClneo (Stratagene), pSG5

(Stratagene), pcDNAI and pcDNAIamp, pcDNA3, pcDNA3.1, pCR3.1 (Invitrogen, San Diego, Calif.), EBO-pSV2-neo (ATCC 37593), pBPV-1 (8-2) (ATCC 37110), pdBPV-MMTneo(342-12) (ATCC 37224), pRSVgpt (ATCC 37199), pRSVneo (ATCC 37198), pCI.neo (Promega), pTRE (Clontech, Palo Alto, Calif.), pV1Jneo, pIREsneo (Clontech, Palo Alto, Calif.), pCEP4 (Invitrogen, San Diego, Calif.), pSC11, and pSV2-dhfr (ATCC 37146). The choice of vector will depend upon cell type in which it is desired to express the γ3 protease substrates, as well as on the level of expression desired, and the like.

Nucleic acid encoding a polypeptide that is a γ3 protease substrate can be expressed in a cell without the use of an expression vector employing, for example, synthetic mRNA or native mRNA. Additionally, mRNA can be translated in various cell-free systems such as wheat germ extracts and reticulocyte extracts, as well as in cell based systems, such as frog oocytes. Introduction of mRNA into cell based systems can be achieved, for example, by microinjection.

Techniques for introducing nucleic acid into an appropriate environment for expression, for expressing the nucleic acid to produce γ3 protease substrate, and for isolating expressed γ3 protease substrate are will known in the art. Examples of such techniques are provided in references such as Ausubel, *Current Protocols in Molecular Biology*, John Wiley, 1987–1998, and Sambrook et al., in *Molecular Cloning, A Laboratory Manual*, $2^{nd}$ Edition, Cold Spring Harbor Laboratory Press, 1989.

The γ3 protease substrate can be employed in assays measuring membrane-bound or detergent-solubilized γ3 protease. Production of cleavage products can be detected by Aβ peptide or hydrophilic moiety product formation.

Assay conditions employing membrane-bound or detergent-solubilized γ3 protease allow for detectable γ3 protease activity. Such conditions include an effective amount of a zwitterionic detergent, a buffer, and an appropriate temperature.

An effective amount of a particular zwitterionic detergent results in detectable cleavage. Suitable detergents and amounts can be determined by evaluating the effect of a particular detergent on γ3 protease activity. Preferred zwitterionic detergents present during the assay are CHAPS and CHAPSO. A preferred percentage of such detergents is about 0.1% to about 0.5%.

An example of a reaction condition allowing for γ3 protease activity is provided as follows: 1.7 μM substrate incubated with cell membranes or detergent solubilized γ3 protease in the presence of 0.25% CHAPSO in buffer (50 mM MES, pH 6.0, 5 mM $MgCl_2$, 5 mM $CaCl_2$, 150 mM KCl) at 37° C. Based on the present disclosure such reaction conditions can be altered to provide a wide range of additional reaction conditions allowing for γ3 protease activity. Preferably, changes to the reaction conditions do not result in a substantial decrease in activity.

γ3 protease activity can be stopped using techniques well known in the art for stopping enzymatic reactions. Preferably, γ3 protease activity is stopped using reagents compatible with subsequent analysis.

Cleavage of γ3 protease substrates can be measured by detecting formation of an Aβ type product or a product containing the hydrophilic moiety. The presence of either of these products can be measured using techniques such as those employing antibodies and radioactive, electrochemiluminescent, or fluorescent labels. If needed or desirable, a purification step enriching the different products may be employed. Examples of purification steps include the use of antibodies, separation gels, and columns. Preferably, substrate cleavage by γ3 protease is assayed for by detecting the presence of Aβ1-40 or Aβ1-42.

A method for detecting substrate cleavage via the detection of Aβ1-40 or Aβ1-42 is described in Clarke & Shearman, 2000, J. Neurosci. Meth. 102:61–68. This methods involves the use of a homogeneous time-resolved fluorescence assay (HIRF). A first antibody that recognizes a central or N-terminal portion of Aβ1-40 and Aβ1-42 is conjugated to XL-665, which serves as a fluorescence acceptor. A second antibody, that specifically recognizes either Aβ1-40 or Aβ1-42, is conjugated to Europium cryptate, which serves as a fluorescent donor. The second antibody does not recognize the intact substrate but rather recognizes a neoepitope that is formed by cleavage of the substrate by γ3 protease. When γ3 protease cleaves the substrate, the neoepitope is formed, thus permitting binding of the second antibody. When the second antibody is bound, the Europium cryptate fluorescent donor and the XL-665 flourescent acceptor are brought close enough together that fluorescence resonance energy tranfer (FRET) can occur between the Europium cryptate and the XL-665. This FRET can be measured by suitable instrumentation and can serve as a measure of substrate cleavage by γ3 protease. FIGS. 5 and 6 illustrate the concepts behind this method.

Figure 1:
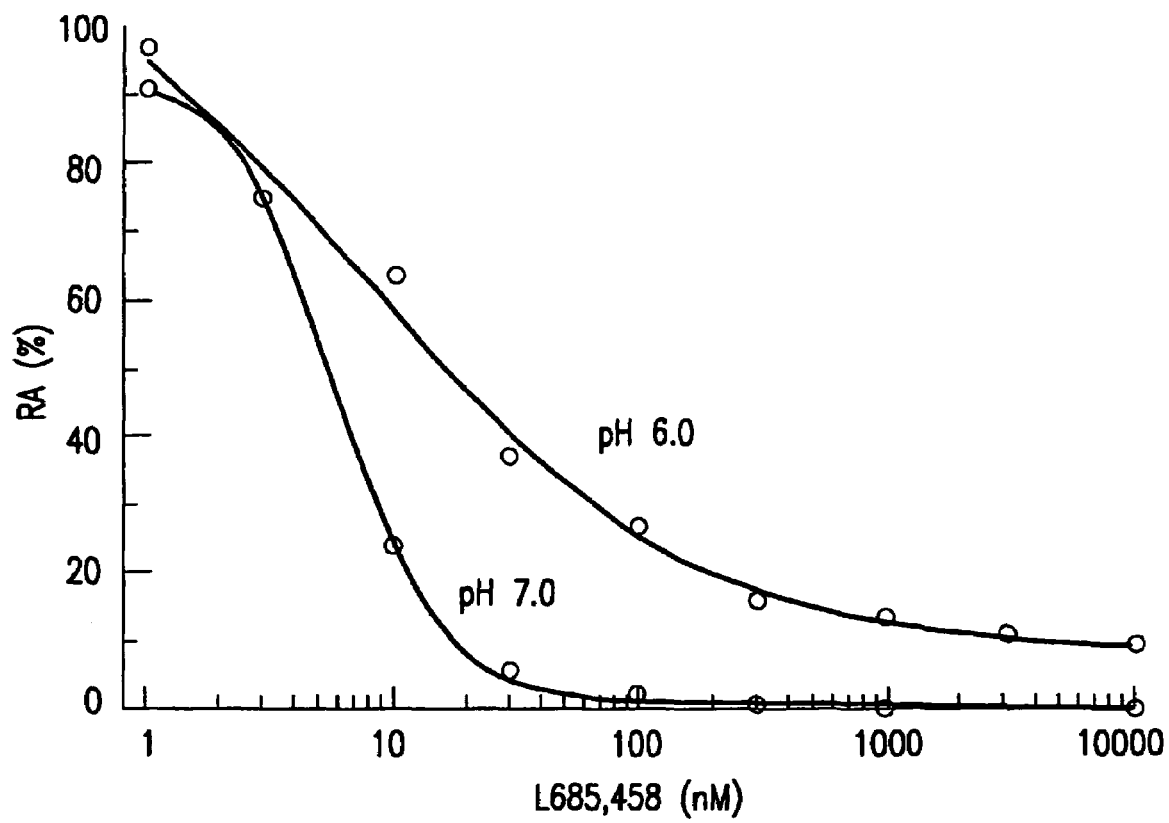
FIG. 1 shows that L-685,458 is able to essentially completely block γ-secretase activity at pH 7.0 (the pH optimum for γ-secretase activity associated with presenilin-1/presenilin-2) but that significant γ-secretase activity remains at pH 6.0 (the pH optimum for γ-secretase activity associated with γ3 protease). The source of γ3 protease was a membrane preparation from HeLa S3 cells prepared as in Example 9. The production of the γ3 protease substrate and the conditions for cleavage are described in Example 10. The procedure for determining whether the substrate had been cleaved by γ3 protease was as in Example 6.
Figure 2A:
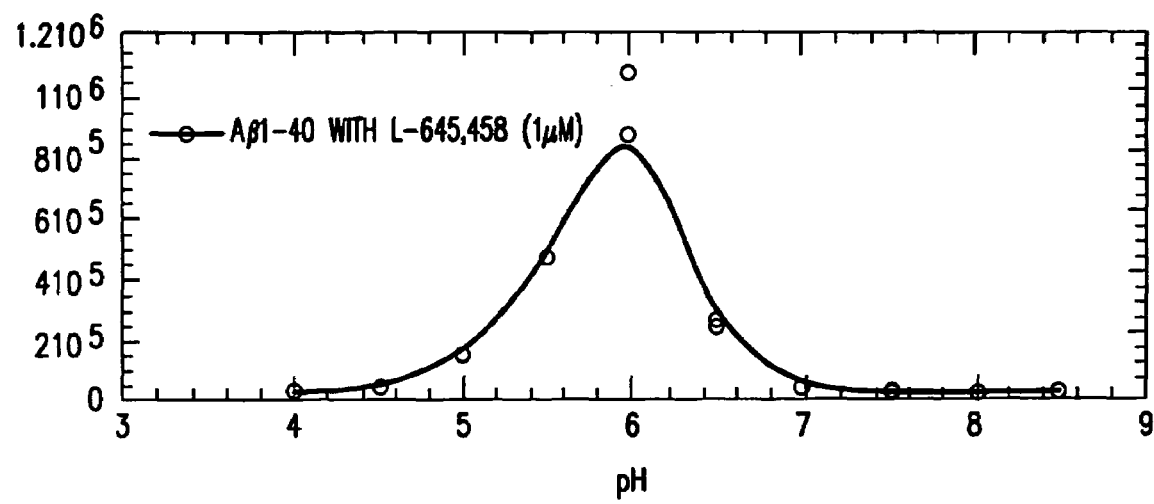
FIG. 2A shows the pH dependency of the generation of Aβ peptide having a length of 40 amino acids (Aβ1-40) in the presence of 1 μM of L-645,458, a concentration sufficient to essentially completely inhibit the γ-secretase activity associated with presenilins 1 and 2. The presence of γ3 protease activity having a pH optimum of about 6 is clearly seen.
Figure 2B:
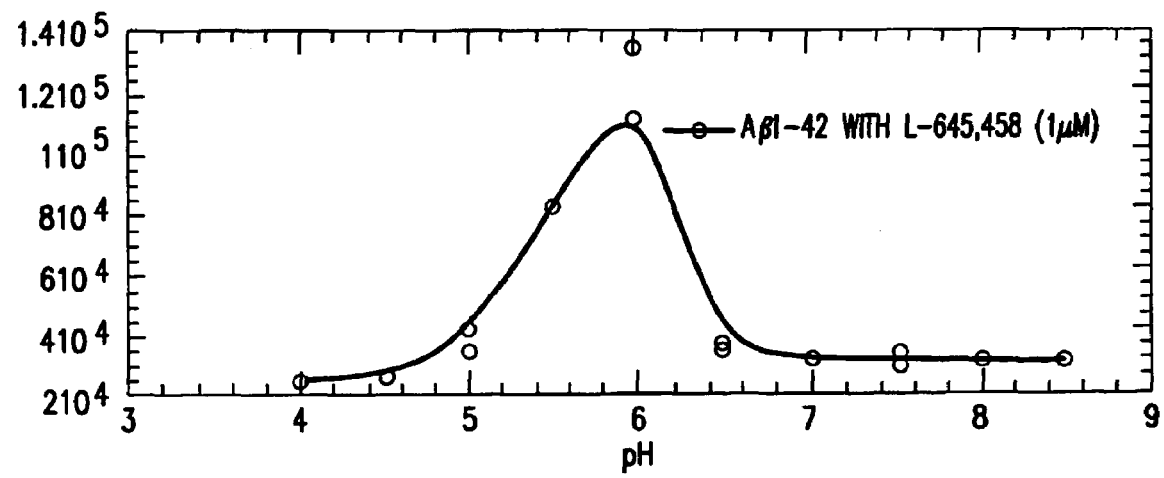
FIG. 2B shows the pH dependency of the generation of Aβ peptide having a length of 42 amino acids (Aβ1-42) in the presence of 1 μM of L-645,458, a concentration sufficient to essentially completely inhibit the γ-secretase activity associated with presenilins 1 and 2. Again, the presence of γ3 protease activity having a pH optimum of about 6 is clearly seen. The source of γ3 protease was ES-PBD18 membranes. ES-PBD18 membranes were prepared from wild-type mouse embryonic stem cells according to the procedure of Example 11.
Figure 3A:
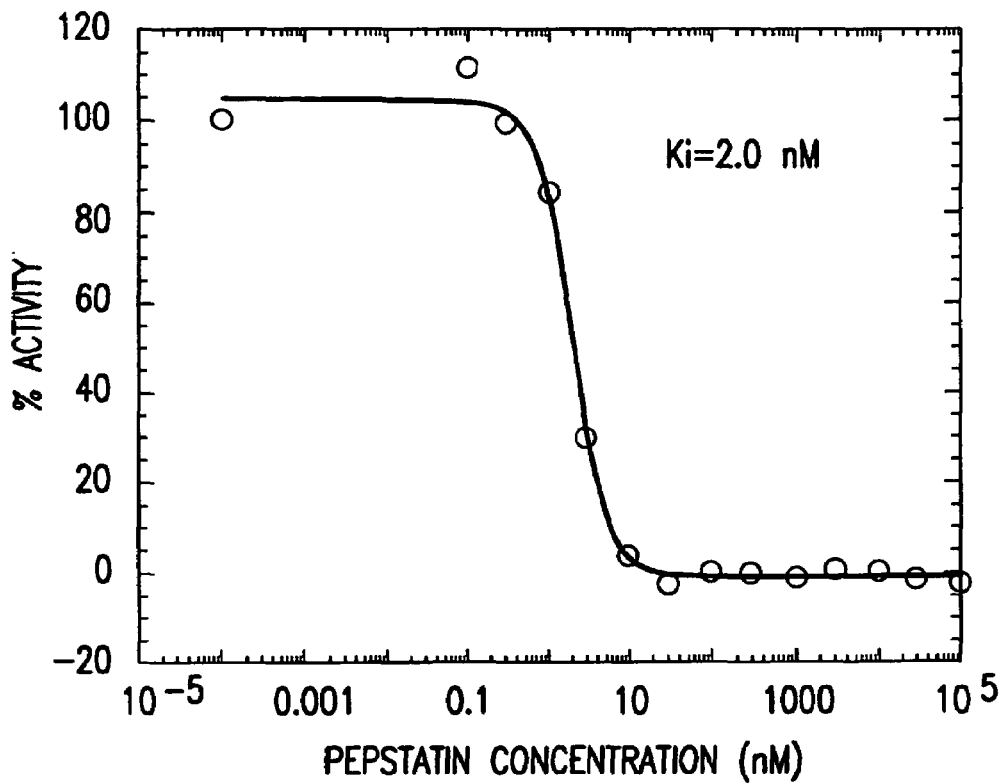
FIG. 3A shows that pepstatin A inhibits the production of Aβ1-40 by γ3 protease.
Figure 3B:
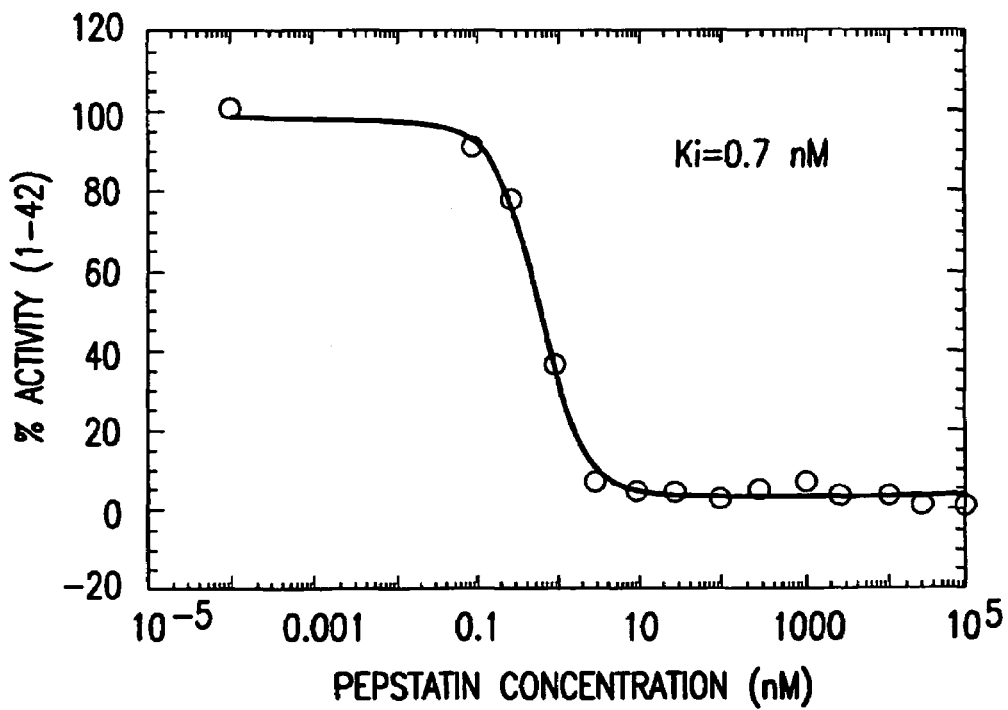
FIG. 3B shows that pepstatin A inhibits the production of Aβ1-42 by γ3 protease.

Another method for product detection, employing electrochemiluminescence with a capture antibody and an antibody specific for either Aβ1-40 or Aβ1-42, is described in Example 6 below. This method was used to obtain the data shown in FIGS. 1–3.

The following non-limiting examples are presented to better illustrate the invention.

EXAMPLE 1

Purification of γ3 Protease-Containing Membranes for Use in Assays

1. Resuspend PS1/PS2 double KO cell pellets (1 ml packed cell volume, ~$2\times10^8$ cells) in 5 ml cold MES buffer (50 mM MES, 5 mM $MgCl_2$, 5 mM $CaCl_2$, 150 mM KCl, pH 6.0 and 1× protease inhibitor cocktails)
2. Pass through French press at 300 psi; repeat one more time. Always wash the French press cylinder with cold $H_2O$ two or three times before using and pass cold buffer through before use. When finished, wash with $H_2O$ until the drainage is clear.
3. Centrifuge the broken cell homogenate at 1,000×g at 4° C. for 10 min. Collect supernatant.
4. Resuspend the pellet from step 3 in 5 ml of fresh buffer using a Douce Homogenizer.
5. Disrupt the membrane pellet with a Dounce homogenizer (10 strokes)
6. Centrifuge at 1,000×g at 4° C. for 10 min. Collect supernatant.
7. Combine supernatants from steps 3 and 6.
8. Centrifuge the combined supernatants at 100,000×g at 4° C. for 1 hr
9. Discard the supernatant from step 8 and resuspend the pellet in 2 ml of buffer (50 mM MES, 5 mM $MgCl_2$, 5 mM $CaCl_2$, 150 mM KCl, pH 6.0 and 1× protease inhibitor cocktails) and centrifuge the resuspended pellet at 100,000×g at 4° C. for 1 hr.
10. Discard the supernatant from step 9 and resuspend the pellet in 2 ml of buffer (50 mM MES, 5 mM $MgCl_2$, 5 mM $CaCl_2$, 150 mM KCl, pH 6.0 and 1× protease inhibitor cocktails) and homogenize with 5 strokes of a Dounce homogenizer.

EXAMPLE 2

Purification of γ3 Protease

Membranes prepared as in Example 1 (e.g., from PS1 and PS2 double knock out mouse cells or HeLa cells) at a protein concentration of 2.5 mg/ml in buffer A (50 mM 2-[N-Morpholino]ethane-sulfonic acid (MES), pH 6.0, 5 mM $MgCl_2$, 5 mM $CaCl_2$, 150 mM KCl, containing "complete" protease inhibitor cocktail (Boehringer Mannheim, Indianapolis, Ind.) are solubilized by treatment with 1% CHAPSO for 60 min at 4° C. and centrifugation at 100,000×g for 60 min. Solubilized proteins are centrifuged at 40,0000 rpm for 1 hr. Supernatant is removed and assayed for enzyme activity. The supernatant is then further diluted 4-fold with MES buffer (50 mM, pH 6.0), resulting in final concentration of 0.25% CHAPSO. A Pepstatin A affinity column is prepared from pepstatin A immobilized agarose (Cat# P-2032, Sigma) and pre-equilibrated with loading buffer (MES 50 mM, pH 6.0) and the supernatant is loaded on the column. The column is washed with three column volumes of loading buffer. Elution buffer (20 mM Tris buffer, pH 7.5) is applied on the column to elute the γ3 protease. The activity of the enzyme is monitored with an in vitro assay. Active fractions are pooled and concentrated on Centracon-10,000.

EXAMPLE 3

PS-1/PS-2 Double Knockout Cells

Such cells can be derived from embryonic stem (ES) cells obtained from the embryos of the founders from cross breeding transgenic mice (PS1 knock-out and PS2 knock-out mice). ES cells were cultured in 90% DMEM, 10% CALF serum, with 1% Penicillin/Streptomycin medium at 37° C., 5% $CO_2$, humidified incubator.

Methods of preparing PS-1/PS-2 double knockout cells are described in Herreman et al., 2000, Nature Cell Biol. 2:461–462.

EXAMPLE 4

Cloning of γ3 Protease

Isolated γ3 protease prepared according to Example 2 is run out on an SDS-PAGE gel and the purity of the enzyme is evaluated by staining with Coomassie blue. A preparative gel is prepared and the γ3 protease protein bands are cut out and analyzed by peptide mapping. Sequence information is then used for searching protein data bases to identify entries corresponding to γ3 protease. Upon obtaining the sequence of the protein from the databases, degenerate oligonucleotide primers are designed and used for PCR against specific tissue cDNA libraries. The amplified DNA bands are sequenced and full-length cDNA clones obtained. DNA encoding γ3 protease is then cloned into suitable host cells to overexpress the protein. Large scale purification can then be carried out to obtain enough protein for further characterization.

EXAMPLE 5

Recombinant production of the γ3 protease substrate

A DNA fragment encoding amino acids 596–695 of the 695 amino acid isoform of APP (APP695) and SEQ.ID.NO.:6 at the C-terminus was generated by PCR amplification of APP695 cDNA using appropriate primers. The employed primers had the following sequences:

GGAATTCCATATGGATGCAG AATTCCGACA (SEQ. ID. NO.: 8) TG; and

CGCGGATCCCTATTTATCGTCATCGTCTTTG (SEQ. ID. NO.: 9) TAGTCGTTCTGCATCTGCTCAAAGAACTTG

The Met that serves as the translation start site is residue 596 of APP695 (the P1 residue with respect to the γ3 protease cleavage site). This DNA fragment was inserted into the procaryotic expression vector pET2-21b (Novagen, Madison, Wis.). The recombinant protein of SEQ.ID.NO.:7 was overproduced in *E. coli* [strain BL21(DE3)] and purified by Mono-Q column chromatography (Pharmacia Biotech).

SEQ.ID.NO.:10 provides a nucleic acid sequence encoding the recombinant protein of SEQ.ID.NO.:7 along with a stop codon.

ATGGATGCAGAATTCCGACATGACTCAGGATA (SEQ. ID. NO.: 10)

TGAAGTTCATCATCAAAAATTGGTGTTCTTTG

CAGAAGATGTGGGTTCAAACAAAGGTGCAATC

ATTGGACTCATGGTGGGCGGTGTTGTCATAGC

GACAGTGATCGTCATCACCTTGGTGATGCTGA

AGAAGAAACAGTACACATCCATTCATCATGGT

GTGGTGGAGGTTGACGCCGCTGTCACCCCAGA

GGAGCGCCACCTGTCCAAGATGCAGCAGAACG

GCTACGAAAATCCAACCTACAAGTTCTTTGAG

CAGATGCAGAACGACTACAAAGACGATGACGA

TAAATAG

EXAMPLE 6

Detection of the Aβ Peptide Products of γ3 Protease Activity by Electrochemiluminescence (ECL)

Aβ peptides were detected using a sandwich assay employing an antibody to capture the peptide and an antibody to detect the presence of the peptide. Detection was achieved by using electrochemiluminescence (ECL) (Yang et al., 1994, Bio/Technology 12:193–194; Khorkova et al., 1998, J. Neurosci. Meth. 82:159–166) and an Origen 1.5 Analyzer (Igen Inc., Gaithersburg, Md.).

Capture was performed using the 4G8 murine monoclonal antibody (Senetek PLC, Maryland Heights, Mo.). The 4G8 murine monoclonal antibody binds an epitope in the Aβ peptide (about amino acids 18–21 of SEQ.ID.NO.:3) that is immediately distal to the α-secretase cleavage site. The 4G8 monoclonal antibody was biotinylated with Biotin-LC-Sulfo-NHS-Ester (Igen Inc., Gaithersburg, Md.).

Detection was achieved using the G2-10 murine monoclonal antibody and the FCA3542 rabbit antibody. The G2-10 murine monoclonal antibody (provided by K. Beyreuther, University of Heidelberg, Germany) binds the C-terminus that is exposed after γ3 protease-mediated cleavage to generate amino acid 40 of the Aβ1-40 peptide. (Ida et al., 1996, J. Biol. Chem. 271:22908–22914). The FCA3542 rabbit antibody (provided by F. Checler, IPMC du CNRS, Valbonne, France) binds the C-terminus that is exposed after γ3 protease-mediated cleavage to generate amino acid 42 of the Aβ1-42 peptide. (Barelli et al., 1997, Mol. Med. 3:695–707.)

The G2-10 and FCA3542 antibodies were ruthenylated with TAG-NHS Ester (Igen Inc., Gaithersburg, Md.). Aβ(x-40) was detected with biotinylated 4G8 and ruthenylated G2-10. Aβ(x-42) was detected with biotinylated 4G8 and ruthenylated FCA3542.

EXAMPLE 7

γ3 Protease Assay Using Artificial Substrate

In vitro assays measuring γ3 protease activity are performed using γ3 protease that is isolated by the method described in Example 2. Alternatively, membranes prepared as in Example 1 may be used. SEQ.ID.NO.:7 substrate (1.7 μM) is incubated with isolated γ3 protease (50 nM) in presence of detergent in buffer B (50 mM MES, pH 6.0, 5 mM $MgCl_2$, 5 mM $CaCl_2$, 150 mM KCl) at 37° C. Generally, 0.25% CHAPSO is provided as the detergent. The reactions are stopped by adding RIPA (150 mM NaCl, 1.0% NP-40, 0.5% DOC, 0.1% SDS, 50 mM Tris HCl, pH 8.0). The samples are centrifuged at 1,000 g for 1 min and the supernatant solutions are assayed for the Aβ peptides by ECL. The Aβ1-40- and Aβ1-42-related products from γ3 protease-mediated processing of SEQ.ID.NO.:7 substrate possess a Met at the N-terminus and are thus defined as M-Aβ1-40 and M-Aβ1-42, respectively.

EXAMPLE 8

L-685,458

L-685,458 is a γ-secretase inhibitor having the following structure:

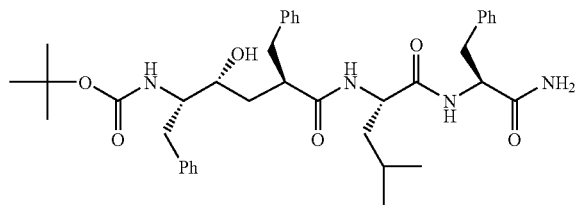

L-685,458 contains an hydroxyethylene dipeptide isostere and is thought to function as a transition state analog mimic of aspartyl proteases (Shearman et al., 2000, Biochemistry 39:8698–8704). L-685,458 was prepared as follows: {1S-Benzyl-4-R-[1-(1S-carbamoyl-2-phenylethylcarbamoyl)-1S-3-methylbutylcarbamoyl]-2R-hydroxy-5-phenylpentyl}carbamic acid tert-butyl ester (L-685,458) was prepared by the coupling of 2R-benzyl-5S-tert-butoxycarbonylamino-4R-(tert-butyldimethylsilanyloxy)-6-phenylhexanoic acid (Evans et al., 1985, J. Org. Chem. 50:4615–4625) with Leu-Phe-NH2 followed by deprotection with tetrabutylammonium fluoride. The synthesis of {1S-benzyl-4-R-[1-(1S-carbamoyl-2-phenylethylcarbamoyl)-1S-3-methylbutylcarbamoyl]-2S-hydroxy-5-phenylpentyl}carbamic acid tert-butyl ester (L-682,679) has been described previously (De Solms et al., 1991, J. Med. Chem. 34:2852–2857). {1S-Benzyl-4-R-[1-(1S-carbamoyl-2-phenylethylcarbamoyl)-1S-3-methylbutylcarbamoyl]-2-oxo-5-phenylpentyl}carbamic acid tert-butyl ester (L-684,414) was prepared by pyridinium dichromate-mediated oxidation of L-682,679.

EXAMPLE 9

Membranes Containing γ3 Protease from HeLa Cells

HeLa S3 cells from American Type Culture Collection (Rockville, Md.) were grown in bioreactors (Analytical Biological Services; Wilmington, Del.) in 90% DMEM, 10% fetal bovine serum, 2 mM glutamine and 100 μg/ml each of penicillin and streptomycin. Frozen HeLa S3 cells were resuspended in buffer A (50 mM 2-[N-Morpholino] ethane-sulfonic aid, MES) MES, pH 6.0, 5 mM $MgCl_2$, 5 mM $CaCl_2$, 150 mM KCl) containing "complete" protease inhibitor cocktail (Boehringer Mannheim, Indianapolis, Ind.). The cells were broken by single-pass through a French Press (Spectronic Instruments, Rochester, N.Y.). Cell debris and nuclei were removed by centrifugation at 800×g for 10 min. The supernatant solutions were centrifuged at 100,000×g for 60 min. The ensuing pellets were resuspended by Dounce homogenizer in buffer A and the centrifugation was repeated. The final membrane pellets were resuspended by Douce homogenizer in buffer A to yield a protein concentration of approximately 12 mg/ml. All procedures were performed at 4° C. The membranes were stored at −70° C.

EXAMPLE 10

Production of γ3 Protease Substrate and Conditions for Cleavage by γ3 Protease

A DNA fragment encoding amino acids 596–695 of the 695 amino acid isoform of APP (APP695) and the Flag sequence (DYKDDDDK (SEQ.ID.NO.:6) at the C-terminus was generated by PCR amplification with suitably-designed oligonucleotides and the APP695 cDNA. The Met that serves as the translation start site is residue 596 of APP695 (the P1 residue with respect to the β-secretase cleavage site). This DNA fragment was inserted into the procaryotic expression vector pET2-21b (Novagen, Madison Wis.). The recombinant protein, C100Flag (SEQ.ID.NO.:7), was overproduced in E. coli [strain BL21(DE3)] and purified by Mono-Q column chromatography (Pharmacia Biotech). C100Flag (1.7 μM) was incubated with cell membranes (0.5 mg/ml) in presence of CHAPSO, CHAPS or Triton X-100 (0, 0.125, 0.25, 0.5, or 1%) in buffer B (50 mM 1,4-piperazinediethanesulfonic acid (PIPES), pH 7.0, 5 mM $MgCl_2$, 5 mM $CaCl_2$, 150 mM KCl) at 37° C. The reactions were stopped by adding RIPA (150 mM NaCl, 1.0% NP-40, 0.5% sodium deoxycholate, 0.1% SDS, 50 mM Tris HCl, pH 8.0) and boiling for 5 min. The samples were centrifuged and the supernatant solutions were assayed for the Aβ peptides by electrochemiluminescence (ECL). The Aβ1-40- and Aβ1-42-related products from γ3 protease-mediated processing of C100Flag possess a Met at the N-terminus and are thus defined as M-Aβ1-40 and M-Aβ1-42, respectively. Supernatant solution from CHAPSO-extracted HeLa cell membranes (solubilized γ3 protease) was incubated with C100Flag in buffer B containing 0.25% CHAPSO and subsequently assayed for M-Aβ1-40 and M-Aβ1-42 using ECL.

EXAMPLE 11

Production of Membranes Containing γ3 Protease from Wild-Type Mouse Embryonic Stem Cells 1. Resuspend pellet (2–10 ml, ~$10^8$–$10^9$ cells) in 2× volume of cold MES buffer (50 mM (2-[N-Morpholino]ethanesulfonic aid (MES), 5 mM $MgCl_2$, 5 mM $CaCl_2$, 150 mM KCl, pH 6.0) plus 1× Protease Inhibitor Cocktail (#1836153, complete Mini protease inhibitor cocktail, Roche).
2. Homoginize pellet using Douce homogenizer at 4° C., 20 times.
3. Spin at "2000" rpm, 4° C., 10 min. Collect supernatant.
4. Resuspend pellet in 5–10 ml fresh cold MES buffer using Douce homogenizer, homogenize 10×, spin at 2000 rpm, 4° C., 10 min. Collect supernatant.
5. Combine supernatant from step 3 and 4, balance, ultra centrifuge at 35K, 4° C., 1 hr.
6. Discard the supernatant, resuspend pellet in 5 ml MES buffer using Dounce homogenizer, ultra centrifuge at 35K, 4° C., 30 min.
7. Discard supernatant, resuspend pellet in 1–3 ml MES buffer, homogenize 5×, check protein concentration, and save in liquid nitrogen.

EXAMPLE 12

Gel Exclusion Chromatography of γ3 Protease

Gel exclusion chromatography was performed as follows: solubilized γ3 protease was diluted 4-fold in buffer (50 mM PIPES, pH 7.0, 5 mM $MgCl_2$, 5 mM $CaCl_2$, 150 mM KCl) and 1 ml was loaded onto a Superose 6 HR 10/30 column (Pharmacia Biotech) using an AKTAexplorer chromatography system (Pharmacia Biotech). The column was eluted with buffer B containing 0.25% CHAPSO. Fractions (0.5 ml) were analyzed for in vitro γ3 protease activity as described herein.

EXAMPLE 13

Transition-State Analogue Inhibitors γ-Secretase Activity

Esler et al., 1997, Nature Biotechnology 15:258–263 disclose the γ-secretase inhibitors 1, BrA-1,1-Bt, and BrA-1-Bt, the structures of which are shown below.

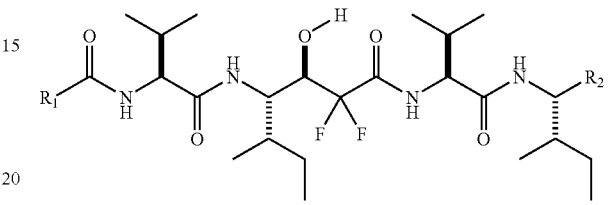

1 $R_1$=t-Bu-O (tert-butoxy); $R_2$=$CO_2Me$
BrA-1 $R_1$=$BrCH_2$; $R_2$=$CO_2Me$
1-Bt $R_1$=t-Bu-O (tert-butoxy); $R_2$=$CH_2O$-Bt (Bt=biotin)
BrA-1-Bt $R_1$=$BrCH_2$; $R_2$=$CH_2O$-Bt (Bt=biotin)

EXAMPLE 14

Additional Transition-State Analogue Inhibitors γ-Secretase Activity

The following γ-secretase inhibitors are disclosed in International Patent Publication WO 01/53255. Example 7 is L-685,458.

| Stucture | Example Number |
|---|---|
| | Example 1 |
| | Example 2 |

-continued
| Stucture | Example Number |
|---|---|
| 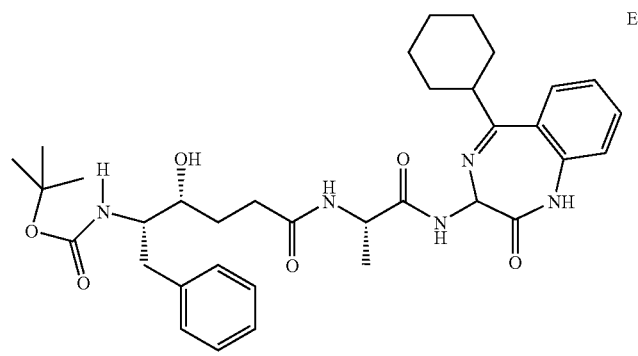 | Example 3 |
| 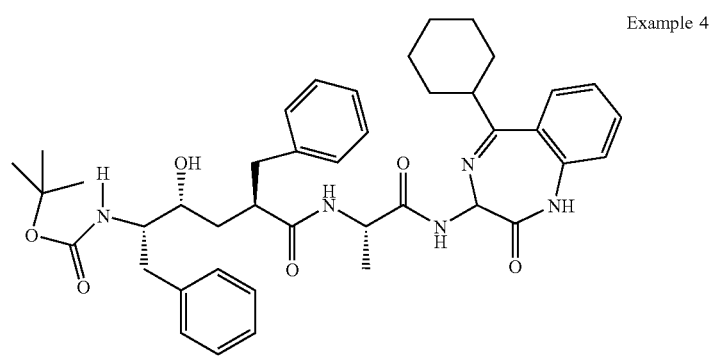 | Example 4 |
| 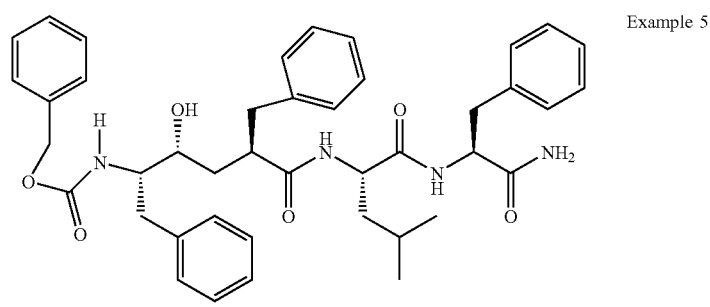 | Example 5 |
| 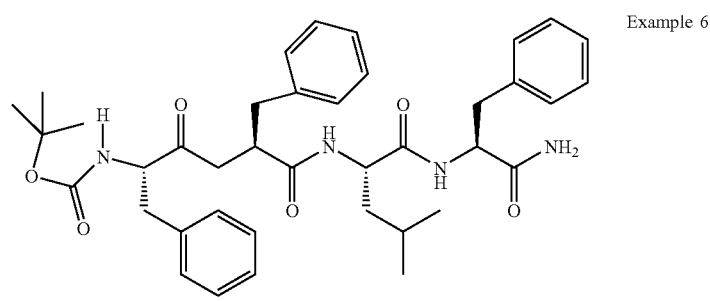 | Example 6 |

-continued

| Structure | Example Number |
|---|---|
| | Example 7 |
| | Example 8 |
| | Example 9 |

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed is:

1. A membrane preparation from eukaryotic cells containing γ3 protease having an $M_r$ of approximately 60 kDa to 120 kDa during gel filtration analysis where the γ3 protease is catalytically active and has an activity that:
   is not susceptible to inhibition by L-685,458;
   is susceptible to inhibition by Pepstatin A;
   displays a pH optimum of 6.0;
   cleaves a substrate having an amino acid sequence comprising SEQ.ID.NO.:3 between positions 40 and 41 of SEQ.ID.NO.:3 or between positions 42 and 43 of SEQ.ID.NO.:3;
   where the membrane preparation has been prepared by a method comprising:
   (a) lysis of cells expressing γ3 protease to produce a lysate;
   (b) low speed centrifugation of the lysate to form a pellet and a supernatant from the lysate;
   (c) high speed centrifugation of the supernatant from step (b) to form a pellet and a supernatant from the supernatant from step (b); and
   (d) resuspension of the pellet from step (c) to form the membrane preparation; and
   (e) determining that the membrane preparation contains catalytically active γ3 protease by incubating the membrane preparation in the presence of a suitable substrate of γ3 protease under suitable conditions such that the γ3 protease cleaves at least a portion of the substrate into product and identifying product produced from the substrate by the γ3 protease.

2. The membranes of claim 1 where the eukaryotic cells are presenilin-1/presenilin-2 double knockout cells or HeLa cells.

3. The membranes of claim 1 where low speed centrifugation is carried out by centrifuging at from about 750×g to about 1,500×g at a temperature of about 2° C. to about 10° C. for about 5 minutes to about 20 minutes and high speed centrifugation is carried out by centrifuging at from about 75,000×g to about 150,000×g at a temperature of about 2° C. to about 10° C. for about 30 minutes to about 90 minutes.

4. The membranes of claim 1 where low speed centrifugation is carried out by centrifuging at about 1,000×g at a temperature of about 4° C. for about 10 minutes and high speed centrifugation is carried out by centrifuging at about 100,000×g at a temperature of about 4° C. to about 60 minutes.

5. The membranes of claim 1 where step (e) is carried out in the presence of an inhibitor of γ-secretase or at a pH of about 5.8 to 6.2.

6. Purified γ3 protease prepared by a method comprising:
   (a) solubilizing the membranes of claim 1 in a zwitterionic detergent;
   (b) centrifuging the solubilizing membranes to obtain a supernatant;
   (c) passing the supernatant over an affinity column to bind γ3 protease in the supernatant to the affinity column;
   (d) eluting γ3 protease from the affinity column.

7. The purified γ3 protease of claim 6 where the zwitterionic detergent is CHAPS or CHAPSO at a concentration of about 1% to 2% (w/v) and the affinity column is a Pepstatin A affinity column.

8. A method of preparing a membrane suspension containing γ3 protease comprising:
   (a) lysis of cells expressing γ3 protease to produce a lysate;
   (b) low speed centrifugation of the lysate to form a pellet and a supernatant from the lysate;
   (c) high speed centrifugation of the supernatant from step (b) to form a pellet;
   (d) resuspension of the pellet from step (c) to form the membrane suspension;
   (e) determining that the membrane suspension from step (d) contains catalytically active γ3 protease is by incubating the membrane suspension in the presence of a suitable substrate of γ3 protease under suitable conditions such that the γ3 protease cleaves at least a portion of the substrate into product and identifying product produced from the substrate by the γ3 protease;
   where the γ3 protease has an $M_r$ of approximately 60 kDa to 120 kDa during gel filtration analysis and has an activity that:
   is not susceptible to inhibition by L-685,458;
   is susceptible to inhibition by Pepstatin A;
   displays a pH optimum of 6.0;
   cleaves a substrate having an amino acid sequence comprising SEQ.ID.NO.:3 between positions 40 and 41 of SEQ.ID.NO.:3 or between positions 42 and 43 of SEQ.ID.NO.:3.

9. The method of claim 8 where step (e) is carried out in the presence of an inhibitor of γ-secretase or at a pH of about 5.8 to 6.2.

10. An assay for γ3 protease comprising:
    (a) providing a source of γ3 protease;
    (b) incubating the γ3 protease in the presence of a suitable substrate under suitable conditions such that the γ3 protease cleaves the substrate into product; and
    (c) determining the amount of product produced from the substrate by the γ3 protease.

11. The assay of claim 10 where step (b) is carried out in the presence of an inhibitor of γ-secretase or at a pH of about 5.8 to 6.2.

12. A method of identifying an inhibitor of γ3 protease comprising:
    (a) incubating:
        (i) a source γ3 protease;
        (ii) a substrate of γ3 protease:
            in the presence and in the absence of a substance;
    (b) determining whether the substrate has been cleaved by the γ3 protease;

where, if the substrate has been cleaved by γ3 protease to a lesser extent in the presence as compared to the absence of the substance, then the substance is an inhibitor of γ3 protease.

13. The method of claim 12 where the source of γ3 protease is a membrane preparation containing γ3 protease.

14. The method of claim 13 where the membrane preparation comprises membranes isolated from eukaryotic cells, the membranes containing γ3 protease having an $M_r$ of approximately 60 kDa to 120 kDa during gel filtration analysis where the γ3 protease is catalytically active and has an activity that:
is not susceptible to inhibition by L-685,458;
is susceptible to inhibition by Pepstatin A;
displays a pH optimum of 6.0;
cleaves a substrate having an amino acid sequence comprising SEQ.ID.NO.:3 between positions 40 and 41 of SEQ.ID.NO.:3 or between positions 42 and 43 of SEQ.ID.NO.:3.

15. The method of claim 12 where the substrate of γ3 protease is a polypeptide comprising all of SEQ.ID.NO.:3;
a polypeptide comprising positions 10–70 of SEQ.ID.NO.:3;
a polypeptide comprising positions 15–65 of SEQ.ID.NO.:3;
a polypeptide comprising positions 20–60 of SEQ.ID.NO.:3;
a polypeptide comprising positions 25–55 of SEQ.ID.NO.:3;
a polypeptide comprising positions 30–50 of SEQ.ID.NO.:3;
a polypeptide comprising positions 31–49 of SEQ.ID.NO.:3;
a polypeptide comprising positions 32–48 of SEQ.ID.NO.:3;
a polypeptide comprising positions 33–47 of SEQ.ID.NO.:3;
a polypeptide comprising positions 34–46 of SEQ.ID.NO.:3;
a polypeptide comprising positions 35–45 of SEQ.ID.NO.:3;
or a polypeptide comprising positions 36–44 of SEQ.ID.NO.:3.

16. The method of claim 12 where the substrate comprises an amino acid sequence selected from the group consisting of: SEQ.ID.NO.:2, SEQ.ID.NO.:3, SEQ.ID.NO.:4, SEQ.ID.NO.:5, and SEQ.ID.NO.:7.

17. The method of claim 13 where the γ3 protease:
has an $M_r$ of approximately 60 kDa to 120 kDa during gel filtration analysis:
is not susceptible to inhibition by L-685,458;
is susceptible to inhibition by Pepstatin A;
displays a pH optimum of 6.0;
cleaves a substrate having an amino acid sequence comprising SEQ.ID.NO.:3 between positions 40 and 41 of SEQ.ID.NO.:3 or between positions 42 and 43 of SEQ.ID.NO.:3.

18. The method of claim 12 where step (a) is carried out in the presence of an inhibitor of γ-secretase or at a pH of about 5.8 to 6.2.

19. The method of claim 18 where the inhibitor of γ-secretase is selected from the group consisting of: L-685, 458, 1, BrA-1, 1-Bt, and BrA-1-Bt.

* * * * *